United States Patent
Han

(10) Patent No.: US 10,867,417 B2
(45) Date of Patent: Dec. 15, 2020

(54) NEURAL NETWORK FOR GENERATING SYNTHETIC MEDICAL IMAGES

(71) Applicant: Elekta, Inc., Atlanta, GA (US)

(72) Inventor: Xiao Han, Chesterfield, MO (US)

(73) Assignee: Elekta, Inc., Atlanta, GA (US)

( * ) Notice: Subject to any disclaimer, the term of this patent is extended or adjusted under 35 U.S.C. 154(b) by 0 days.

(21) Appl. No.: 16/330,648

(22) PCT Filed: Jul. 14, 2017

(86) PCT No.: PCT/US2017/042136
§ 371 (c)(1),
(2) Date: Mar. 5, 2019

(87) PCT Pub. No.: WO2018/048507
PCT Pub. Date: Mar. 15, 2018

(65) Prior Publication Data
US 2019/0362522 A1    Nov. 28, 2019

Related U.S. Application Data

(60) Provisional application No. 62/408,676, filed on Oct. 14, 2016, provisional application No. 62/384,171, filed on Sep. 6, 2016.

(51) Int. Cl.
*G06T 11/00* (2006.01)
*A61B 5/055* (2006.01)
(Continued)

(52) U.S. Cl.
CPC .............. *G06T 11/00* (2013.01); *A61B 5/055* (2013.01); *A61B 5/7267* (2013.01);
(Continued)

(58) Field of Classification Search
CPC ...... G06T 11/00; G06T 11/003; G06T 11/005; G01R 33/5608; G01R 33/56; A61B 5/055;
(Continued)

(56) References Cited

U.S. PATENT DOCUMENTS 6,819,790 B2 * 11/2004 Suzuki .................. G06T 7/0012
382/130
2011/0286649 A1    11/2011 Reisman et al.
(Continued)

FOREIGN PATENT DOCUMENTS

CN    103180878 A    6/2013
CN    105637536 A    6/2016
(Continued)

OTHER PUBLICATIONS

"International Application Serial No. PCT US2017 042136, International Preliminary Report on Patentability dated Mar. 21, 2019", 8 pgs.
(Continued)

*Primary Examiner* — Dwayne D Bost
*Assistant Examiner* — Stephen M Brinich
(74) *Attorney, Agent, or Firm* — Schwegman Lundberg & Woessner, P.A.; Sanjay Agrawal

(57) ABSTRACT

Systems, computer-implemented methods, and computer readable media for generating a synthetic image of an anatomical portion based on an origin image of the anatomical portion acquired by an imaging device using a first imaging modality are disclosed. These systems may be configured to receive the origin image of the anatomical portion acquired by the imaging device using the first imaging modality, receive a convolutional neural network model trained for predicting the synthetic image based on the origin image, and convert the origin image to the
(Continued)

synthetic image through the convolutional neural network model. The synthetic image may resemble an imaging of the anatomical portion using a second imaging modality differing from the first imaging modality.

25 Claims, 18 Drawing Sheets

(51) Int. Cl.
    *A61B 5/00*     (2006.01)
    *G01R 33/56*     (2006.01)
    *A61B 6/03*     (2006.01)
    *G01R 33/48*     (2006.01)
    *A61B 8/00*     (2006.01)

(52) U.S. Cl.
    CPC ..... *G01R 33/4812* (2013.01); *G01R 33/5608* (2013.01); *A61B 6/032* (2013.01); *A61B 6/037* (2013.01); *A61B 8/00* (2013.01); *G01R 33/481* (2013.01); *G01R 33/4814* (2013.01)

(58) Field of Classification Search
    CPC ....... A61B 5/7267; A61B 5/7264; A61B 6/03; A61B 6/032; A61B 6/037; A61B 8/00
    USPC .......................................... 382/128–132, 100
    See application file for complete search history.

(56) References Cited

U.S. PATENT DOCUMENTS

| | | | |
|---|---|---|---|
| 2013/0121549 | A1 | 5/2013 | Pekar et al. |
| 2014/0212013 | A1 | 7/2014 | Han |
| 2016/0093048 | A1 | 3/2016 | Chen |
| 2016/0148371 | A1 | 5/2016 | Itu et al. |
| 2018/0150947 | A1* | 5/2018 | Lu ........................ G06N 3/0454 |

FOREIGN PATENT DOCUMENTS

| | | |
|---|---|---|
| CN | 110234400 A | 9/2019 |
| JP | 2019534634 A | 11/2019 |
| RU | 2544479 | 3/2015 |
| WO | WO-2015144540 A1 | 10/2015 |
| WO | 2015171056 | 11/2015 |
| WO | WO-2016036516 A1 | 3/2016 |
| WO | WO-2016092394 A1 | 6/2016 |
| WO | WO-2018048507 A1 | 3/2018 |
| WO | WO-2018209438 A1 * 11/2018 ........... A61B 5/0066 |

OTHER PUBLICATIONS

"Australian Application Serial No. 2017324069, First Examination Report dated Jun. 12, 2019", 6 pgs.
Miao, S, "A CNN Regression Approach for Real-Time 2D 3D Registration", IEEE Transactions on Medical Imaging, vol. 35, No. 5, (May 2016), 1352-1363.
"International Application Serial No. PCT/US2017/042136, International Search Report dated Oct. 25, 2017", 3 pgs.
"International Application Serial No. PCT/US2017/042136, Written Opinion dated Oct. 25, 2017", 6 pgs.
"Australian Application Serial No. 2017324069, Response filed Dec. 4, 2019 to First Examination Report dated Jun. 12, 2019", 20 pgs.
"European Application Serial No. 17751509.5, Response to Communication pursuant to Rules 161(1) and 162 EPC filed Nov. 4, 2019", 18 pgs.
"Japanese Application Serial No. 2019-534634, Notification of Reasons for Refusal dated Dec. 17, 2019", 10 pgs.
Li, Rongjian, et al., "Deep Learning Based Imaging Data Completion for Improved Brain Disease Diagnosis", Med Image Comput Comput Assist Interv, vol. 17, pt. 3, (2014), 305-312.
Matsuo, Yotaka, "The future of artificial intelligence and the emerging potentials of date sharing", Information Management, vol. 58, No. 8, (2015), 597-605.
Miao, Shun, et al., "Real-Time 2D/3D Registration via CNN Regression", Cornell University arXiv.org > cs > arXiv:1507.07505, (2015), 5 pgs.
Tokui, Masaya, "Deep learning concept from the viewpoint of optimization", Operations Research, vol. 60, No. 4,, (Apr. 1, 2015), 191-197.
"European Application Serial No. 17751509.5, Communication Pursuant to Article 94(3) EPC dated Mar. 10, 2020", 4 pgs.
"European Application Serial No. 17751509.5, Communication Pursuant to Rule 114(2) EPC dated Feb. 21, 2020", 68 pgs.
"Chinese Application Serial No. 201780065652.5, Office Action dated Apr. 8, 2020", 19 pgs.
"Japanese Application Serial No. 2019-534634, Response filed May 15, 2020 to Notification of Reasons for Refusal dated Dec. 17, 2019", w/ English claims, 25 pgs.
"European Application Serial No. 17751509.5, Response filed Sep. 21, 2020 to Communication dated Jul. 6, 2020", 27 pgs.
"Chinese Application Serial No. 201780065652.5, Response filed Aug. 24, 2020 to Office Action dated Apr. 8, 2020", w/. English claims, 67 pgs.
"European Application Serial No. 17751509.5, Communication dated Jul. 6, 2020", 131 pgs.
"Japanese Application Serial No. 2019-534634, Final Notification of Reasons for Refusal dated Jun. 6, 2020", 5 pgs.
"Japanese Application Serial No. 2019-534634, Response filed Jul. 3, 2020 to Final Notification of Reasons for Refusal dated Jun. 16, 2020", w/ English claims, 12 pgs.
Cicek, Ozgun, et al., "3D U-Net: Learning Dense Volumetric Segmentation from Sparse Annotation", (Jun. 21, 2016), 8 pgs.
Haacke, E Mark, "Magnetic Resonance Imaging Physical Principles and Sequence Design", 65 pgs.
Hounsfield, G. N., "Computerized transverse axial scanning (tomography): Part I. Description of System", British Journal of Radiology, 46, (Dec. 1973), 1016-1022.

* cited by examiner

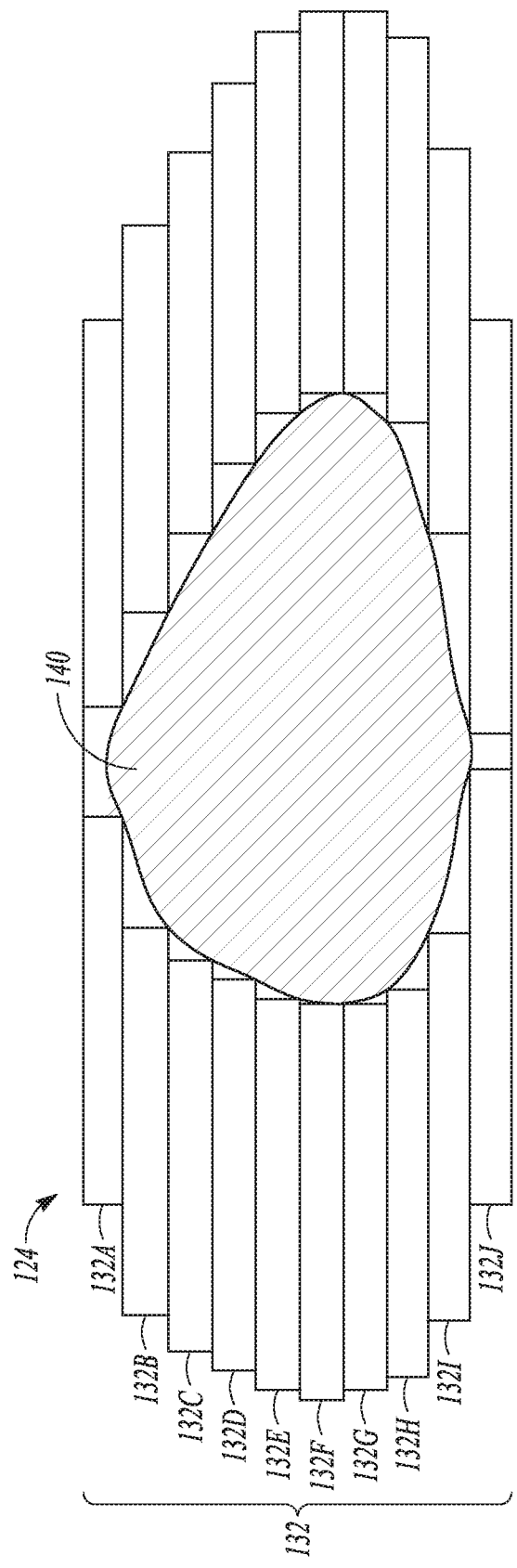

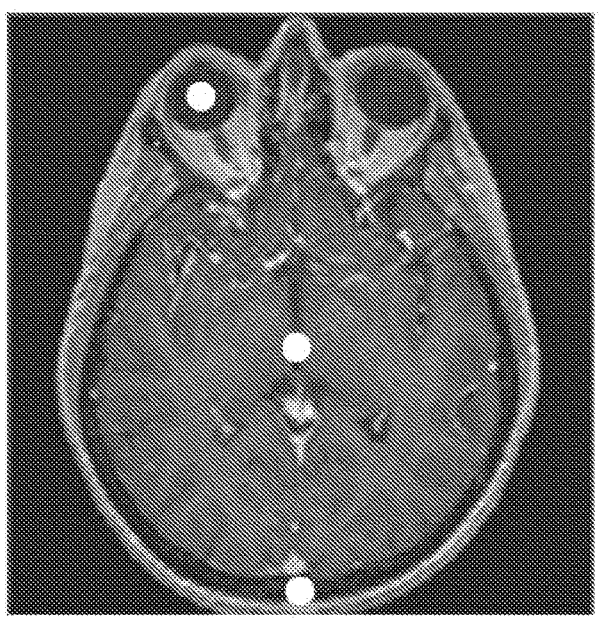 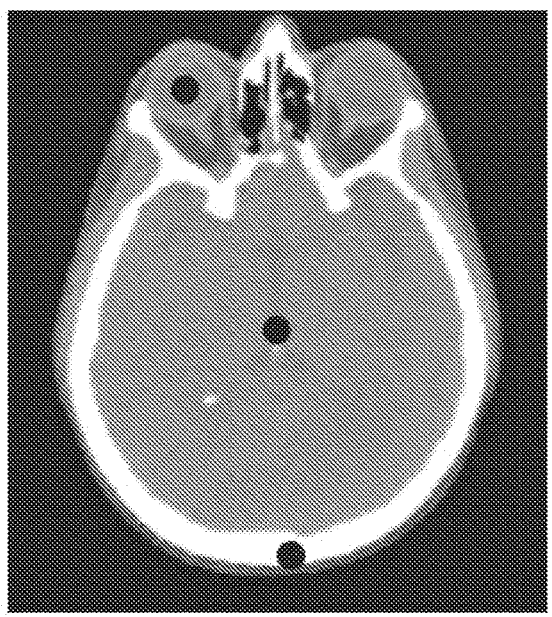
*FIG. 4A*  *FIG. 4B*

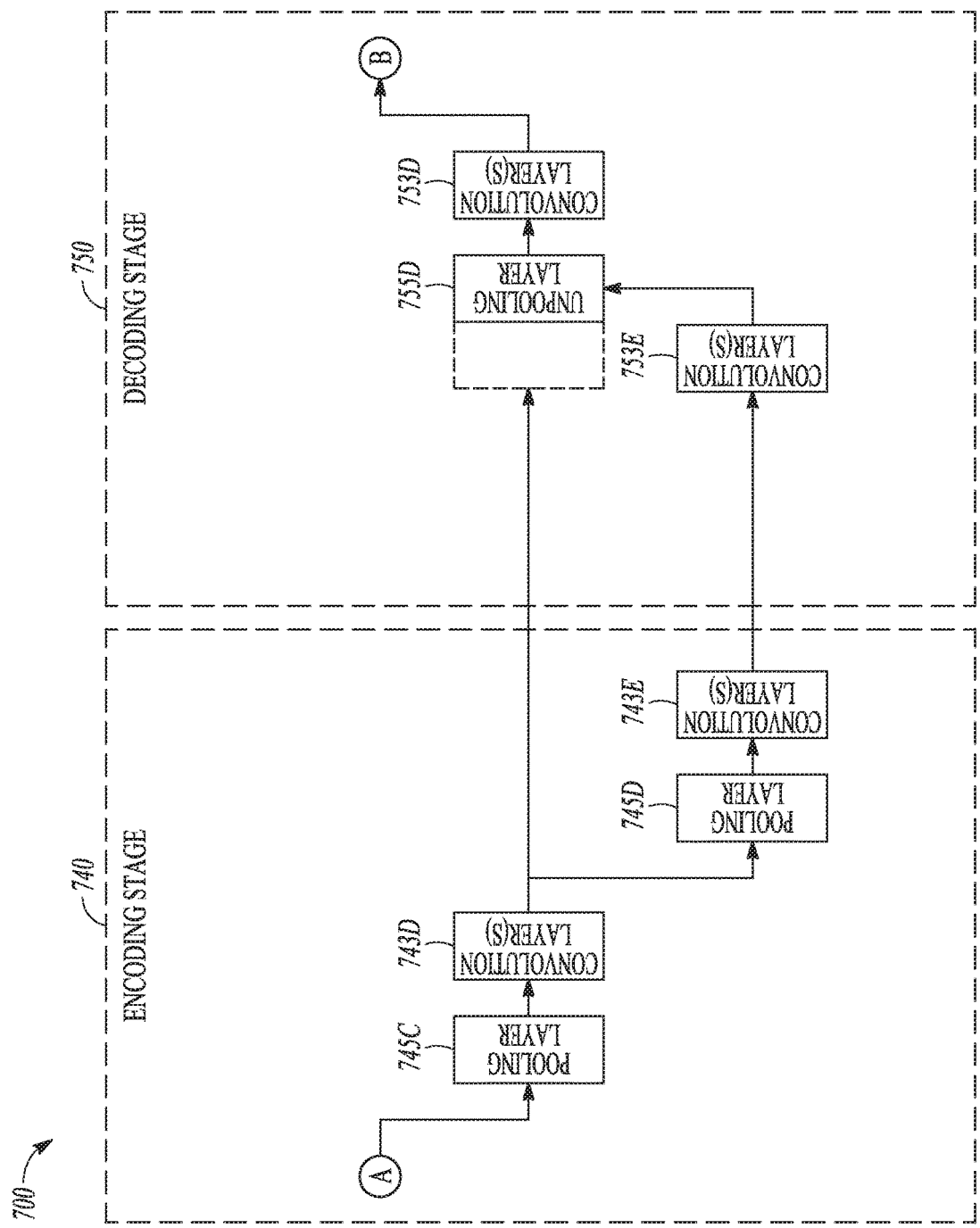

NEURAL NETWORK FOR GENERATING SYNTHETIC MEDICAL IMAGES

CROSS REFERENCE TO RELATED APPLICATIONS

This application is a U.S. National Stage Filing under 35 U.S.C. 371 from International Application No. PCT/US2017/042136, filed on Jul. 14, 2017, and published as WO2018/048507 on Mar. 15, 2018, which claims the benefit of priority from U.S. Provisional Patent Application No. 62/384,171 filed on Sep. 6, 2016 and U.S. Provisional Patent Application No. 62/408,676 filed on Oct. 14, 2016, the benefit of priority of each of which is hereby claimed herein, and which applications and publication are hereby incorporated herein by reference in their entirety.

TECHNICAL FIELD

This disclosure generally relates to generating synthetic images using machine learning algorithms for use in radiation therapy. More specifically, this disclosure relates to systems and methods for generating computed tomography (CT) images from Magnetic Resonance Imaging (MRI) images using neural networks.

BACKGROUND

CT imaging has been traditionally used as the primary source of image data in the planning process of external radiation therapy. CT images offer accurate representation of patient geometry, and CT values can be directly converted to electron densities for radiation dose calculation. However, because conventional CT images are generated through use of an imaging radiation source, using CT may expose a patient to additional radiation dosages. In recent years, interest in replacing CT images with MRI image in the radiotherapy treatment planning process has emerged. This is due to the fact that MRI is free of ionizing radiation and provides a superior soft tissue contrast for more accurate target and structure delineation. MRI also captures functional information of the human body, such as tissue metabolism and functionality. However, MRI intensity values are not directly related to electron densities and conventional MRI sequences cannot obtain MRI signal from bone. Therefore, it is beneficial if a "pseudo CT image" or a "synthetic image," such as a pseudo or synthetic CT image (referred to herein as a "synthetic CT image"), could be derived from an acquired MRI image.

A synthetic CT image derived from an MRI image can be used to facilitate patient dose computation in radiation therapy treatment planning or to generate digitally-reconstructed radiographs for image guidance. The synthetic CT image may also be used for patient positioning during radiotherapy. Therefore, it is desirable to accurately generate a synthetic CT image using MRI image data in order for patients to be spared from additional radiation exposure arising from CT imaging. Preferably, a synthetic CT image would accurately resemble a "real" CT image that is acquired by a CT scanner. In other words, a synthetic CT should be as close as possible to the real CT image, e.g., in terms of relative voxel intensity values and contrast features. Generating accurate synthetic CT image is not a simple task because there does not exist a direct mathematical relationship between CT image intensity values (CT numbers) and MRI intensity values.

Existing methods for automatic synthetic CT image generation can be roughly classified into three categories: tissue classification-based approaches, atlas-based approaches, and model-based approaches. Tissue classification or tissue segmentation methods first classify the MRI image into regions of different tissue types (e.g., air, fat, soft tissue, or bone), and then use bulk density assignments to assign a different CT number for each tissue type. Automatic tissue segmentation is a difficult problem, especially if using traditional MRI images. For instance, bone and air are inseparable or indistinguishable in traditional MRI images. Thus, more sophisticated MRI sequences (e.g., MRI images capable of acquiring images of a higher resolution) are often needed for more accurate tissue segmentation. Even if tissue segmentation is possible, dividing the anatomy into few tissue types provides a very coarse approximation of the actual anatomy. For example, prostate and bladder are both soft tissues, but their CT intensities are usually different.

Atlas-based approaches are also known as registration-based approaches. In the context of synthetic CT generation, the term "atlas" often refers to a dataset comprising paired atlas MRI and CT images. In an example, the pairing of MRI and CT images can be performed by image registration. To generate a synthetic CT image from a given original MRI image, an atlas-based method first aligns each atlas MRI image from the "atlas" to the original MRI image through computing an image registration transformation (usually deformable or nonlinear image registration is needed, instead of a simple linear registration). The computed registration transformation can then be applied to map the corresponding atlas CT image to the original MRI image, and generate a deformed atlas CT. The deformed atlas CT image provides an estimation of the real CT image (e.g., a synthetic CT image).

Normally, to achieve better accuracy, multiple deformed atlas CTs are computed, and the multiple deformed atlas CTs can be combined together, such as by averaging, to generate a final synthetic CT image corresponding to the original MRI image. However, most existing image registration methods can handle only single-channel MRI images. Also, if a large number of atlases are used, because the original MRI image has to be registered to each atlas MRI image, the computation time may be increased. The process is slow because these techniques require continuous access to the full atlas database, for the image registration operations involve all (atlas selection—can use less than all the images) the atlas MRI images and atlas CT images. In an example, atlas selection can be used to select a subset of all the atlas MRI images and atlas CT images.

Model-based or learning-based approaches aim to build a predictive model from available training data. Once the predictive model has been trained, it can then be applied to any new MRI image of the same type (e.g., any new MRI image acquired using an MRI sequence that is the same as that used to acquire the training data.) in order to predict a corresponding CT image. The training process typically uses a supervised learning algorithm. Specifically, a supervised learning algorithm uses a known set of input data and known responses or outputs to that data, and then trains a model to generate reasonable predictions for the response to new data. For synthetic CT prediction, a regression (instead of classification) model is needed since the response variables (e.g., the CT values) are real numbers. Existing model-based approaches and traditional learning algorithms also require extraction of certain types of "features" to use as inputs to the model. Existing methods differ in the type of features each method may use as an input to its regression model.

These existing methods also require manually designed features. Furthermore, existing methods predict the CT number of a single voxel. Thus, these methods must be applied in a sliding window fashion (e.g., by applying a model to a series of sub-regions of an image), or voxel-by-voxel fashion, to generate a complete synthetic CT image. Such sliding window approaches often require significant computing time and resources in order to generate a complete synthetic CT image.

Accordingly, there is a need for new systems and methods using artificial intelligence techniques to generate synthetic CT images from other images, such as MRI images.

SUMMARY

In an aspect, the disclosure can feature a computer-implemented method for generating a synthetic image of an anatomical portion based on an origin image of the anatomical portion acquired by an imaging device using a first imaging modality. The method can include receiving the origin image of the anatomical portion acquired by the imaging device using the first imaging modality, and receiving a convolutional neural network model trained for predicting the synthetic image based on the origin image. The method can also include converting, by at least one processor, the origin image to the synthetic image through the convolutional neural network model. The synthetic image can resemble a second imaging modality depiction of the anatomical portion wherein the second imaging modality can differ from the first imaging modality. The first imaging modality can be Magnetic Resonance Imaging, and the second imaging modality can be Computed Tomography. The first imaging modality and the second imaging modality are selected from the group of Magnetic Resonance Imaging, Computed Tomography, ultrasound imaging, Positron Emission Tomography, and Single-Photon Emission Computed Tomography. The method can also include receiving a plurality of training origin images acquired using the first imaging modality, receiving a plurality of training destination images acquired using the second imaging modality, wherein each training destination image can correspond to a training origin image, determining a convolutional neural network architecture, and training the convolutional neural network model using the training origin images and corresponding training destination images. The origin image can be a two-dimensional image and the synthetic image can be a two-dimensional image. The origin image can include a stack of two-dimensional images and the synthetic image can include a corresponding stack of two-dimensional images. The origin image can be a three-dimensional volume and the synthetic image can be a three-dimensional volume. The origin image can be a three-dimensional image, and generating the synthetic image can include selecting a plurality of stacks of adjacent two-dimensional images from the three-dimensional image, converting each stack of adjacent two-dimensional images to a stack of synthetic two-dimensional images using the convolutional neural network model, and determining, by the at least one processor, the synthetic image by aggregating the stacks of synthetic two-dimensional images. The origin image can be a three-dimensional image, and generating the synthetic image can include creating a first stack of two-dimensional images from a first plane of the three-dimensional image and a second stack of two-dimensional images from a second plane of the three-dimensional image, converting the first stack and the second stack of two-dimensional images to a first stack and a second stack of synthetic two-dimensional images using the convolutional neural network model, and determining the synthetic image by aggregating the first stack and the second stack of synthetic two-dimensional images. The adjacent two-dimensional images can be in the same plane and carry dependent structure information in an axis orthogonal to the plane. The plurality of stacks of adjacent two-dimensional images can partially overlap, and aggregating the stacks of synthetic two-dimensional images can include averaging overlapping synthetic two-dimensional images. Converting the first stack of two-dimensional images to the first stack of synthetic two-dimensional images can use a first convolutional neural network model, and converting the second stack of two-dimensional images to the second stack of synthetic two-dimensional images can use a second convolutional neural network model. The first convolutional neural network model and the second convolutional neural network model can correspond to two different anatomical planes. The origin image can include multi-channel images of the anatomical portion acquired using different acquisition settings or using different acquisition channels of the imaging device. The multi-channel images can include T1-weighted Magnetic Resonance images and T2-weighted Magnetic Resonance images. The convolutional neural network model can include a first component configured to determine a feature map of the origin image and a second component configured to determine the synthetic image from the feature map. The first component can include a plurality of encoding layers and the second component includes a plurality of decoding layers. The first component can be configured to reduce the size of the feature map through down-sampling, and the second component can be configured to increase the size of the feature map through up-sampling. The convolutional neural network can include a plurality of convolutional layers, wherein the set of model parameters can include learnable filter weights used by the plurality of convolutional layers. The convolutional neural network can include 10 to 500 layers. The convolutional neural network model can include converting the training origin images to synthetic images using the convolutional neural network model, determining a difference between the synthetic images and the corresponding training destination images, and updating the set of model parameters of the convolutional neural network model based on the difference. The training can be completed when a difference between the synthetic image and the destination image is smaller than a predetermined threshold. The difference can be measured by a loss function calculated based on the synthetic image and the destination image.

In an aspect, the disclosure can feature a system for generating a synthetic image of an anatomical portion based on an origin image of the anatomical portion acquired by an imaging device using a first imaging modality. The system can include an input interface configured to receive the origin image of the anatomical portion acquired by the imaging device using the first imaging modality, and to receive a convolutional neural network model trained for predicting the synthetic image based on the origin image. The system can also include at least one storage device configured to store the origin image and the convolutional neural network model. The system can also include an image processor configured to convert the origin image to the synthetic image through the convolutional neural network model. The synthetic image (e.g., a pseudo-CT image) can be stored in the at least one storage device. The synthetic image can resemble a second imaging modality depiction of the anatomical portion, wherein the second imaging modality (e.g., a CT) can differ from the first imaging modality. The origin image can include multi-channel images of the anatomical portion acquired using different acquisition settings or using different acquisition channels of the imaging device. The first imaging modality can be Magnetic Resonance Imaging, and the second imaging modality can be Computed Tomography. The first imaging modality and the second imaging modality can be selected from among the group of Magnetic Resonance Imaging, Computed Tomography, ultrasound imaging, Positron Emission Tomography, and Single-Photon Emission Computed Tomography. The input interface can be further configured to receive a plurality of training origin images acquired using the first imaging modality, receive a plurality of training destination images acquired using the second imaging modality, wherein each training destination image can correspond to a training origin image. The image processor can be further configured to train the convolutional neural network model using the training origin images and corresponding training destination images. The origin image can be a two-dimensional image and the synthetic image can be a two-dimensional image. The origin image can include a stack of two-dimensional image and the synthetic image can include a corresponding stack of two-dimensional images. The origin image can be a three-dimensional volume and the synthetic image can be a three-dimensional volume. The origin image can be a 3D image and the image processor can be further configured to select a plurality of stacks of adjacent two-dimensional images from the 3D image, convert each stack of adjacent two-dimensional images to a stack of synthetic two-dimensional images using the convolutional neural network model, determine the synthetic image by aggregating the stacks of synthetic two-dimensional images. The adjacent two-dimensional images can be in the same plane and can carry dependent structure information in an axis orthogonal to the plane. The plurality of stacks of adjacent two-dimensional images can partially overlap, and aggregating the stacks of synthetic two-dimensional images can include averaging overlapping synthetic two-dimensional images. The origin image can be a three-dimensional image and the image processor can be further configured to create a first stack of two-dimensional images from a first plane of the three-dimensional image and a second stack of two-dimensional images from a second plane of the three-dimensional image, convert the first stack and the second stack of two-dimensional images to a first stack and a second stack of synthetic two-dimensional images using the convolutional neural network model, and determine the synthetic image by aggregating the first stack and the second stack of synthetic two-dimensional images. The image processor can be configured to convert the first stack of two-dimensional images to the first stack of synthetic two-dimensional images using a first convolutional neural network model, and convert the second stack of two-dimensional images to the second stack of synthetic two-dimensional images using a second convolutional neural network model, wherein the first convolutional neural network model and the second convolutional neural network model can correspond to two different anatomical planes. The origin image can include multi-channel images of the anatomical portion acquired using different acquisition channels of the imaging device. The multi-channel images can include T1-weighted Magnetic Resonance images and T2-weighted Magnetic Resonance images. The convolutional neural network model can include a first component configured to determine a feature map of the origin image and a second component configured to determine the synthetic image from the feature map. The first component can include a plurality of encoding layers and the second component includes a plurality of decoding layers. The first component can be configured to reduce the size of the feature map through down-sampling, and the second component can be configured to increase the size of the feature map through up-sampling. The convolutional neural network can include a plurality of convolutional layers, wherein the set of model parameters can include learnable filter weights used by the plurality of convolutional layers. The convolutional neural network can include 10 to 500 layers. The image processor can be further configured to convert the training origin images to synthetic images using the convolutional neural network model, determine a difference between the synthetic images and the corresponding training destination images, and update the set of model parameters based on the difference. The difference can be measured by a loss function calculated based on the synthetic images and the corresponding training destination images.

In an aspect, the disclosure can feature a non-transitory computer-readable medium containing instructions that, when executed by at least one processor, cause the at least one processor to perform a method for generating a synthetic image of an anatomical portion based on an origin image of the anatomical portion acquired by an imaging device using a first imaging modality. The method can include receiving the origin image of the anatomical portion acquired by the imaging device using the first imaging modality, and receiving a convolutional neural network model trained for predicting the synthetic image based on the origin image. The method can also include converting the origin image to the synthetic image through the convolutional neural network model. The synthetic image can resemble a second imaging modality depiction of the anatomical portion, wherein the second imaging modality (e.g., a CT) can differ from the first imaging modality. The method can also include receiving a plurality of training origin images acquired using the first imaging modality, receiving a plurality of training destination images acquired using the second imaging modality, each training destination image corresponding to a training origin image, determining a convolutional neural network architecture, and training the convolutional neural network model using the training origin images and corresponding training destination images. The origin image can be a three-dimensional image, and generating the synthetic image can further include selecting a plurality of stacks of adjacent two-dimensional images from the three-dimensional image, converting each stack of adjacent two-dimensional images to a stack of synthetic two-dimensional images using the convolutional neural network model, and determining, by the at least one processor, the synthetic image by aggregating the stacks of synthetic two-dimensional images. The adjacent two-dimensional images can be in the same plane and carry dependent structure information in an axis orthogonal to the plane. The plurality of stacks of adjacent two-dimensional images can partially overlap, and aggregating the stacks of synthetic two-dimensional images can include averaging overlapping synthetic two-dimensional images. The origin image can be a three-dimensional image, and generating the synthetic image can include creating a first stack of two-dimensional images from a first plane of the three-dimensional image and a second stack of two-dimensional images from a second plane of the three-dimensional image, converting the first stack and the second stack of two-dimensional images to a first stack and a second stack of synthetic two-dimensional images using the convolutional neural network model, and determining the synthetic image by aggregating the first stack and the second stack of synthetic two-dimensional images. Converting the first stack of two-dimensional images to the first stack of synthetic two-dimensional images can include using a first convolutional neural network model, and converting the second stack of two-dimensional images to the second stack of synthetic two-dimensional images can include using a second convolutional neural network model. The first convolutional neural network model and the second convolutional neural network model can correspond to two different anatomical planes. The origin image can include multi-channel images of the anatomical portion acquired using different acquisition channels of the imaging device. The multi-channel images can include T1-weighted Magnetic Resonance images and T2-weighted Magnetic Resonance images. The convolutional neural network model can include a first component configured to determine a feature map of the origin image and a second component configured to determine the synthetic image from the feature map. The first component can include a plurality of encoding layers and the second component can include a plurality of decoding layers. The first component can be configured to reduce the size of the feature map through down-sampling, and the second component can be configured to increase the size of the feature map through up-sampling. The convolutional neural network can include a plurality of convolutional layers, wherein the set of model parameters can include learnable filter weights used by the plurality of convolutional layers. The convolutional neural network can include 10 to 500 layers. Training the set of model parameters of the convolutional neural network model can include converting the training origin images to synthetic images using the convolutional neural network model, determining a difference between the synthetic images and the corresponding training destination images, and updating the set of model parameters based on the difference. The difference can be measured by a loss function calculated based on the synthetic images and the corresponding training destination images.

In an aspect, the disclosure can feature a computer-implemented method for generating a convolutional neural network model for predicting a synthetic image of an anatomical portion based on an origin image of the anatomical portion acquired by an imaging device using a first imaging modality. The method can include receiving a plurality of training origin images acquired using the first imaging modality. The method can also include receiving a plurality of training destination images acquired using a second imaging modality, each training destination image corresponding to a training origin image. The method can also include training, by at least one processor, a set of model parameters of the convolutional neural network model using the training origin images and corresponding training destination images. The first imaging modality can be Magnetic Resonance Imaging, and the second imaging modality can be Computed Tomography. The first imaging modality and the second imaging modality can be selected from among the group of Magnetic Resonance Imaging, Computed Tomography, ultrasound imaging, Positron Emission Tomography, and Single-Photon Emission Computed Tomography. The training origin images can include multi-channel images of the anatomical portion acquired using different acquisition channels of the imaging device. The multi-channel images can include T1-weighted Magnetic Resonance images and T2-weighted Magnetic Resonance images. The convolutional neural network model can include a first component configured to determine a feature map of the origin image and a second component configured to determine the synthetic image from the feature map. The first component can include a plurality of encoding layers and the second component includes a plurality of decoding layers. The first component can be configured to reduce the size of the feature map through down-sampling, and the second component can be configured to increase the size of the feature map through up-sampling. The convolutional neural network can include a plurality of convolutional layers, and the set of model parameters can include learnable filter weights used by the plurality of convolutional layers. The convolutional neural network can include 10 to 500 layers. Training the set of model parameters of the convolutional neural network model can include converting the training origin images to synthetic images using the convolutional neural network model, determining a difference between the synthetic images and the corresponding training destination images, and updating the set of model parameters based on the difference. The difference can be measured by a loss function calculated based on the synthetic images and the corresponding training destination images.

Additional objects and advantages of the embodiments will be set forth in part in the description that follows, and in part will be obvious from the description, or may be learned by practice of the embodiments. It is to be understood that both the foregoing general description and the following detailed description are exemplary and explanatory only and are not restrictive of the claims.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus.

BRIEF DESCRIPTION OF THE DRAWINGS

The accompanying drawings, which are incorporated in and constitute a part of this specification, illustrate the disclosed embodiments and, together with the description, serve to explain the disclosed principles. In the drawings:

FIG. 2 illustrates an orthogonal view of an exemplary multi-leaf collimator configuration for shaping, directing, or modulating an intensity of a radiation therapy beam.

FIGS. 4A and 4B depict the differences between an exemplary MRI image and a corresponding CT image.

FIGS. 7D and 7E depict an exemplary convolutional neural network, used by the image conversion system shown in FIG. 5, according to some embodiments of the present disclosure.

DETAILED DESCRIPTION

Figure 1A:
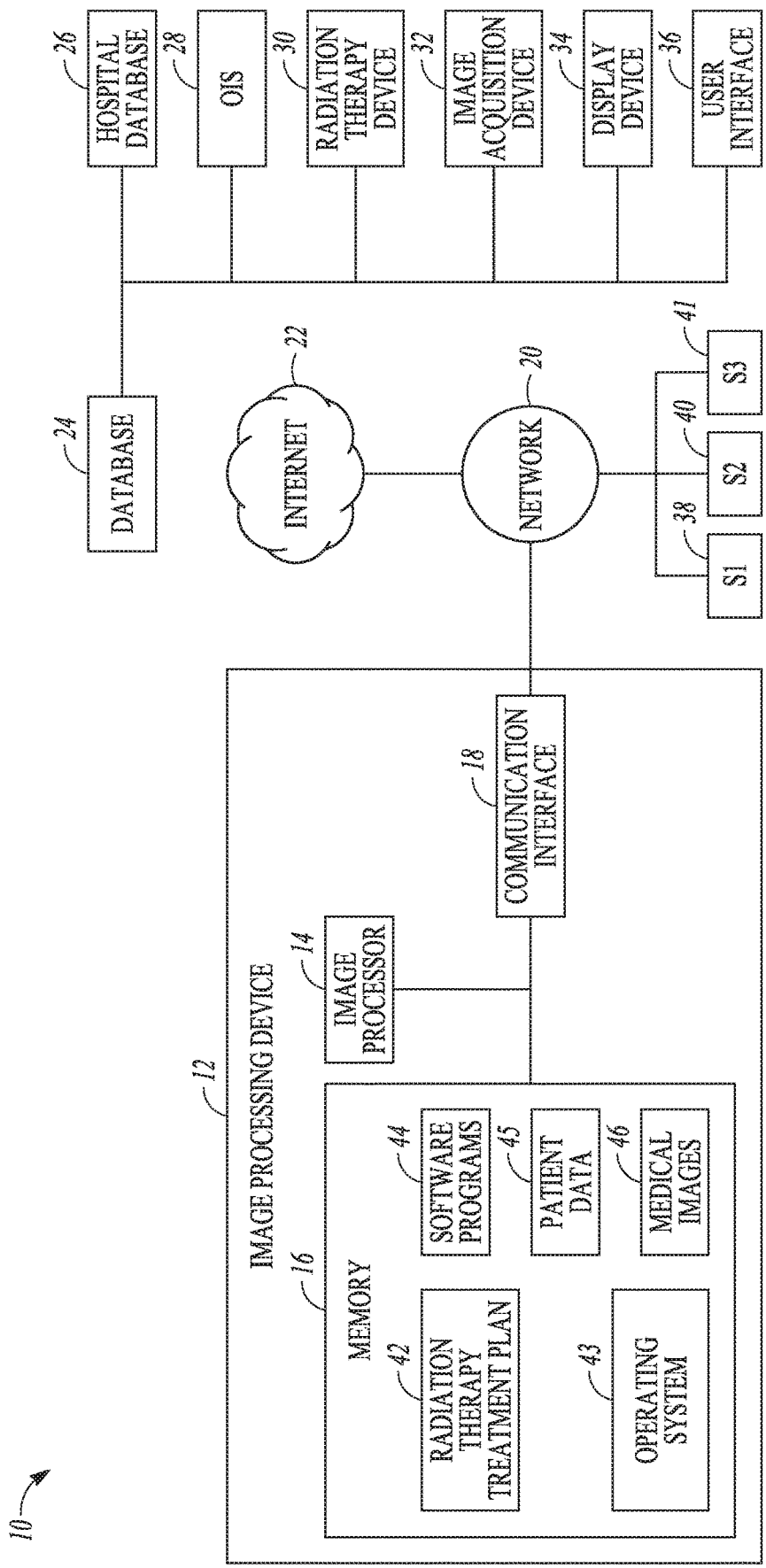
FIG. 1A illustrates an exemplary radiotherapy system, according to some embodiments of the present disclosure.

Reference will now be made in detail to the exemplary embodiments with reference to the accompanying drawings. Wherever possible, the same reference numbers will be used throughout the drawings to refer to same or like parts. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. Also, the words "comprising," "having," "containing," and "including," and other similar forms are intended to be equivalent in meaning and be interpreted as open ended, in that, an item or items following any one of these words is not meant to be an exhaustive listing of such item or items, or meant to be limited to only the listed item or items. And the singular forms "a," "an," and "the" are intended to include plural references, unless the context clearly dictates otherwise. The term "exemplary" is used in the sense of "example," rather than "ideal."

The disclosed embodiments use limited data to initialize the convolutional neural network using parameters of existing neural networks trained for image classification, taking advantage of the principle of transfer learning. The disclosed embodiments advantageously may not require inter-subject image registration, either linear or deformable, and may directly learn the mapping between the MRI images and the corresponding CT images. The disclosed embodiments may advantageously offer better accuracy than an atlas-based method using patch refinement and fusion. This is because the atlas-based method usually relies on patch comparison to find similar atlas candidates, as also common in other atlas- or patch-based methods proposed in the literature. A small, local patch has limited image information. Therefore, using raw image intensities of a patch as features may suffer from large redundancy in the data and reduce the discrimination power. In contrast, the disclosed embodiments may advantageously automatically learn a hierarchy of image features at different scales and complexity levels from a full image.

One or more methods consistent with the disclosed embodiments have been tested on 18 patients, and the results compare favorably with other reported results in the literature, such as results obtained using existing fuzzy c-means clustering methods, methods using atlases for registration, methods using a Gaussian mixture regression model, and atlas registration followed by patch fusion. In addition to improving accuracy, the disclosed embodiments also result in a shorter computation time at deployment. For example, even if training a model (e.g., a deep convolutional neural network (DCNN)) can take days, the training only needs to be done once and acceleration of the training process is possible through the use of multiple GPUs, cloud computers, or super-computers. Applying the trained model to create synthetic images for a new patient may take only a few seconds on a single GPU. In comparison, existing model-based or atlas-based methods can take much longer (for example, minutes or hours).

The disclosed embodiment can also accommodate a large quantity (hundreds of pairs of origin and destination images) of training data. Neural networks can greatly benefit from large amounts of data due to high model capacity. Thus, the accuracy of the disclosed embodiments may increase as additional training data becomes available. Increasing the amount of training data may increase training time, but the size of the final neural network and the synthetic image generation time may remain the same. In contrast, increasing the training data using existing atlas-based methods or other model-based methods (such as existing Gaussian process models) may be impractical, because these existing methods require retention of all training data. In addition, the computation time of these methods is often directly proportional to the number of atlases used. Furthermore, the accuracy of atlas-based methods can quickly saturate, and, as a result, an atlas selection procedure is often required to avoid degradation in accuracy when using a large number of atlases. However, the use of increased training data may increase the accuracy of the final synthetic image generated by the trained neural network model.

FIG. 1A illustrates an exemplary radiotherapy system 10 for providing radiation therapy to a patient. The radiotherapy system 10 includes an image processing device, 12. The image processing device 12 may be connected to a network 20. The network 20 may be connected to the Internet 22. The network 20 can connect the image processing device 12 with one or more of a database 24, a hospital database 26, an oncology information system (OIS) 28, a radiation therapy device 30, an image acquisition device 32, a display device 34, and a user interface 36. The image processing device 12 is configured to generate radiation therapy treatment plans 16 to be used by the radiation therapy device 30.

The image processing device 12 may include a memory device 16, a processor 14 and a communication interface 18. The memory device 16 may store computer-executable instructions, such as an operating system 43, a radiation therapy treatment plans 42 (e.g., original treatment plans, adapted treatment plans and the like), software programs 44 (e.g., artificial intelligence, deep learning, neural networks, radiotherapy treatment plan software), and any other computer-executable instructions to be executed by the processor 14. In an embodiment the software programs 44 may be convert medical images of one format (e.g., MRI) to another format (e.g., CT) by producing synthetic images, such as a pseudo-CT image. For instance, the software programs 44 may include image processing programs to train a predictive model for converting a medial image 46 in one modality (e.g., an MRI image) into a synthetic image of a different modality (e.g., a pseudo CT image); alternatively, the trained predictive model may convert a CT image into an MRI image. The memory device 16 may store data, including medical images 46, patient data 45, and other data required to create and implement a radiation therapy treatment plan 42.

In addition to the memory 16 storing the software programs 44, it is contemplated that software programs 44 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 44 when downloaded to image processing device 14 may be executed by image processor 14.

The processor 14 may be communicatively coupled to the memory device 16, and the processor 14 may be configured to execute computer executable instructions stored thereon. The processor 14 may send or receive medical images 46 to memory 16. For example, the processor 14 may receive medical images 46 from the image acquisition device 32 via the communication interface 18 and network 18 to be stored in memory 16. The processor 14 may also send medical images 46 stored in memory 16 via the communication interface 18 to the network 20 be either stored in database 24 or the hospital database 26.

Further, the processor 14 may utilize software programs 44 (e.g., a treatment planning software) along with the medical images 46 and patient data 45 to create the radiation therapy treatment plan 42. Medical images 46 may include information such as imaging data associated with a patient anatomical region, organ, or volume of interest segmentation data. Patient data 45 may include information such as (1) functional organ modeling data (e.g., serial versus parallel organs, appropriate dose response models, etc.); (2) radiation dosage data (e.g., dose-volume histogram (DVH) information; or (3) other clinical information about the patient and course of treatment (e.g., other surgeries, chemotherapy, previous radiotherapy, etc.).

In addition, the processor 14 may utilize software programs to generate intermediate data such as updated parameters to be used, for example, by a neural network model; or generate intermediate 2D or 3D image, which may then subsequently be stored in memory 16. The processor 14 may subsequently then transmit the executable radiation therapy treatment plan 42 via the communication interface 18 to the network 20 to the radiation therapy device 30, where the radiation therapy plan will be used to treat a patient with radiation. In addition, the processor 14 may execute software programs 44 to implement functions such as image conversion, image segmentation, deep learning, neural networks, and artificial intelligence. For instance, the processor 14 may execute software programs 44 that train or contour a medical image; such software 44 when executed may train a boundary detector, utilize a shape dictionary.

The processor 14 may be a processing device, include one or more general-purpose processing devices such as a microprocessor, a central processing unit (CPU), a graphics processing unit (GPU), an accelerated processing unit (APU), or the like. More particularly, the processor 14 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 14 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 14 may be a special-purpose processor, rather than a general-purpose processor. The processor 14 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 14 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 14 may also include accelerated processing units such as the Desktop A-4(6,8) Series manufactured by AMD™, the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processor 14 can execute sequences of computer program instructions, stored in memory 16, to perform various operations, processes, methods that will be explained in greater detail below.

The memory device 16 can store medical images 46. In some embodiments, the medical images 46 may include one or more MRI image (e.g., 2D MRI, 3D MRI, 2D streaming MRI, 4D MRI, 4D volumetric MRI, 4D cine MRI, etc), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the medical images 46 may also include medical image data, for instance, training images, and ground truth images, contoured images. In an embodiment, the medical images 46 may be received from the image acquisition device 32. Accordingly, image acquisition device 32 may include a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The medical images 46 may be received and stored in any type of data or any type of format that the image processing device 12 may use to perform operations consistent with the disclosed embodiments. The memory device 12 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processor 14, or any other type of computer device. The computer program instructions can be accessed by the processor 14, read from the ROM, or any other suitable memory location, and loaded into the RAM for execution by the processor 14. For example, the memory 16 may store one or more software applications. Software applications stored in the memory 16 may include, for example, an operating system 43 for common computer systems as well as for software-controlled devices. Further, the memory 16 may store an entire software application, or only a part of a software application, that are executable by the processor 14. For example, the memory device 16 may store one or more radiation therapy treatment plans 42.

The image processing device 12 can communicate with the network 20 via the communication interface 18, which is communicatively coupled to the processor 14 and the memory 16. The Communication interface 18 may provide communication connections between the image processing device 12 and radiotherapy system 10 components (e.g., permitting the exchange of data with external devices). For instance, the communication interface 18 may in some embodiments have appropriate interfacing circuitry to connect to the user interface 36, which may be a hardware keyboard, a keypad, or a touch screen through which a user may input information into radiotherapy system 10.

Communication interface 18 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 18 may include one or more digital and/or analog communication devices that permit image processing device 12 to communicate with other machines and devices, such as remotely located components, via the network 20.

The network 20 may provide the functionality of a local area network (LAN), a wireless network, a cloud computing environment (e.g., software as a service, platform as a service, infrastructure as a service, etc.), a client-server, a wide area network (WAN), and the like. For example, network 20 may be a LAN or a WAN that may include other systems S1 (38), S2 (40), and S3 (41). Systems S1, S2, and S3 may be identical to image processing device 12 or may be different systems. In some embodiments, one or more of systems in network 20 may form a distributed computing/simulation environment that collaboratively performs the embodiments described herein. In some embodiments, one or more systems S1, S2, and S3 may include a CT scanner that obtain CT images (e.g., medical images 46). In addition, network 20 may be connected to internet 22 to communicate with servers and clients that reside remotely on the internet.

Therefore, network 20 can allow data transmission between the image processing device 12 and a number of various other systems and devices, such as the OIS 28, the radiation therapy device 30, and the image acquisition device 32. Further, data generated by the OIS 28 and/or the image acquisition device 32 may be stored in the memory 16, the database 24, and/or the hospital database 26. The data may be transmitted/received via network 20, through communication interface 18 in order to be accessed by the processor 14, as required.

The image processing device 12 may communicate with database 24 through network 20 to send/receive a plurality of various types of data stored on database 24. For example, database 24 may include machine data that is information associated with a radiation therapy device 30, image acquisition device 32, or other machines relevant to radiotherapy. Machine data information may include radiation beam size, arc placement, beam on and off time duration, control points, segments, multi-leaf collimator (MLC) configuration, gantry speed, MRI pulse sequence, and the like. Database 24 may be a storage device. One skilled in the art would appreciate that database 24 may include a plurality of devices located either in a central or a distributed manner.

In some embodiments, database 24 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

Image processor 14 may communicate with database 24 to read images into memory 16 or store images from memory 16 to database 24. For example, the database 24 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, etc.) that the database 24 received from image acquisition device 32. Database 24 may store data to be used by the image processor 14 when executing software program 44, or when creating radiation therapy treatment plans 42. The image processing device 12 may receive the imaging data 46 (e.g., 2D MRI slice images, CT images, 2D Fluoroscopy images, X-ray images, 3D MRI images, 4D MRI images, etc.) either from the database 24, the radiation therapy device 30 (e.g., a MRI-Linac), and or the image acquisition device 32 to generate a treatment plan 42.

In an embodiment, the radiotherapy system 100 can include an image acquisition device 32 that can acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient.

Image acquisition device 32 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 32 can be stored within database 24 as either imaging data and/or test data. By way of example, the images acquired by the imaging acquisition device 32 can be also stored by the image processing device 12, as medical image data 46 in memory 16.

In an embodiment, for example, the image acquisition device 32 may be integrated with the radiation therapy device 30 as a single apparatus (e.g., a MRI device combined with a linear accelerator, also referred to as an "MRI-Linac." Such an MRI-Linac can be used, for example, to determine a location of a target organ or a target tumor in the patient, so as to direct radiation therapy accurately according to the radiation therapy treatment plan 42 to a predetermined target.

The image acquisition device 32 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 32 can acquire a 2D slice in any orientation. For example, an orientation of the 2D slice can include a sagittal orientation, a coronal orientation, or an axial orientation. The processor 14 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 32 in "real-time" while a patient is undergoing radiation therapy treatment, for example, when using the radiation therapy device 30. "Real-time" meaning acquiring the data in at least milliseconds or less.

The image processing device 12 may generate and store radiation therapy treatment plans 42 for one or more patients. The radiation therapy treatment plans 42 may provide information about a particular radiation dose to be applied to each patient. The radiation therapy treatment plans 42 may also include other radiotherapy information, such as beam angles, dose-histogram-volume information, the number of radiation beams to be used during therapy, the dose per beam, and the like.

The image processor 14 may generate the radiation therapy treatment plan 42 by using software programs 44 such as treatment planning software, such as Monaco®, manufactured by Elekta AB of Stockholm, Sweden. In order to generate the radiation therapy treatment plans 42, the image processor 14 may communicate with the image acquisition device 32 (e.g., a CT device, a MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the treatment planning device 110 may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 32 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45 Gy, ≤55 Gy and <54 Gy, respectively). The result of inverse planning may constitute a radiation therapy treatment plan 42 that may be stored in memory 16 or database 24. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 12 can generate a tailored radiation therapy treatment plan 42 having these parameters in order for the radiation therapy device 30 to provide radiotherapy treatment to the patient.

In addition, the radiotherapy system 10 may include a display device 34 and a user interface 36. The display device 34 may include one or more display screens that display medical images, interface information, treatment planning parameters (e.g., contours, dosages, beam angles, etc.) treatment plans, a target, localizing a target and/or tracking a target, or any related information to the user. The user interface 36 may be a keyboard, a keypad, a touch screen or any type of device that a user may input information to radiotherapy system 10. Alternatively, the display device 34 and the user interface 36 may be integrated into a device such as a tablet computer, e.g., Apple iPad®, Lenovo Thinkpad®, Samsung Galaxy®, etc.

Furthermore, any and all components of the radiotherapy system 10 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 12, the OIS 28, the image acquisition device 32 could be implemented as a virtual machine. Given the processing power, memory, and computational capability available, the entire radiotherapy system 10 could be implemented as a virtual machine.

Figure 1B:
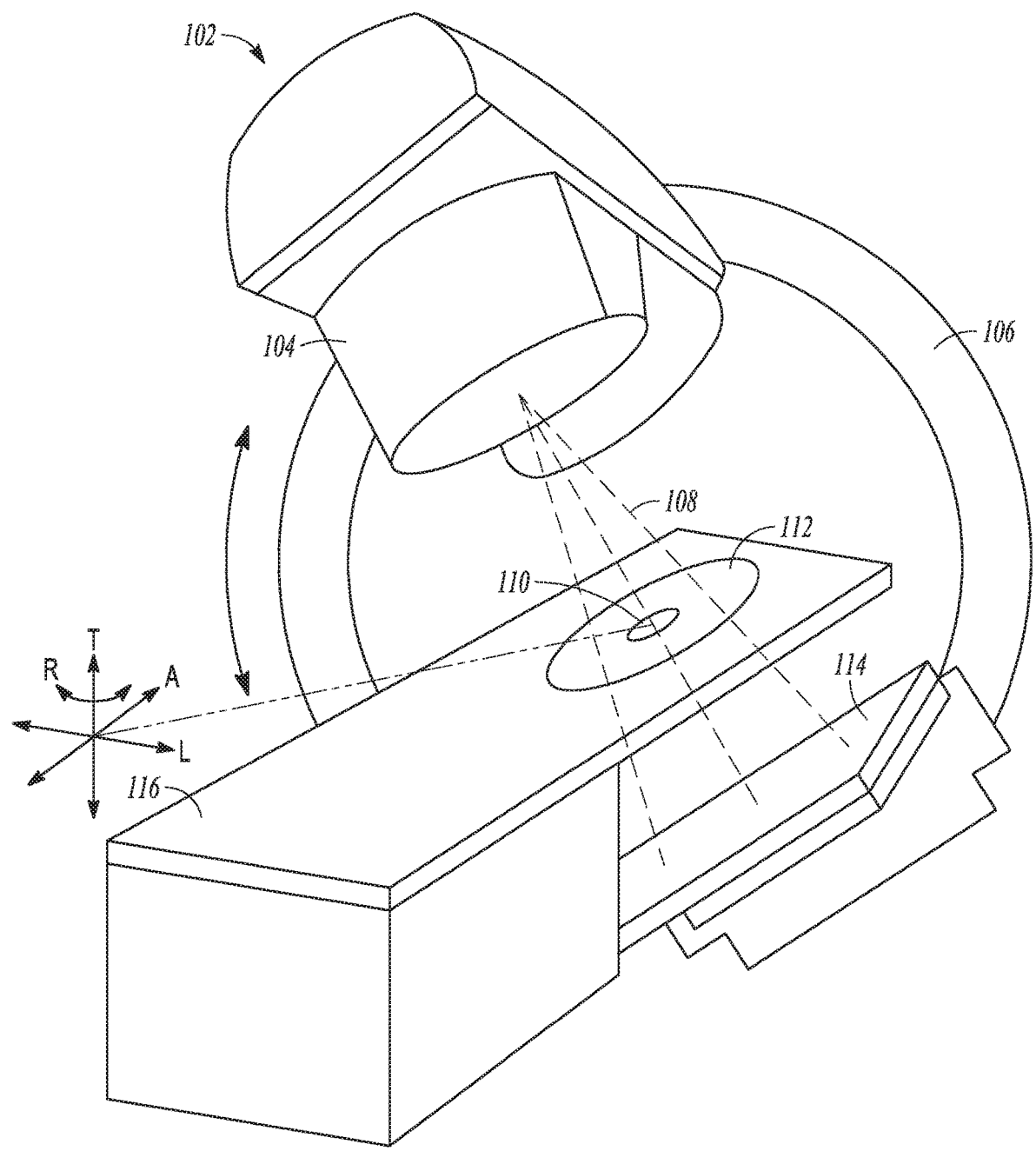
FIG. 1B illustrates an exemplary radiation therapy system that can include radiation therapy output configured to provide a therapy beam.

FIG. 1B illustrates an exemplary radiation therapy device 102 may include a radiation source, such as an X-ray source or a linear accelerator, a multi-leaf collimator (not shown), a couch 116, an imaging detector 114, and a radiation therapy output 104. The radiation therapy device 102 may be configured to emit a radiation beam 108 to provide therapy to a patient. The radiation therapy output 104 can include one or more attenuators or collimators, such as a multi-leaf collimator (MLC) as described in the illustrative example of FIG. 2, below.

Referring back to FIG. 1B, a patient can be positioned in a region 112, using a table or couch 116 to receive a radiation therapy dose according to a radiation therapy treatment plan. The radiation therapy output 104 can be mounted or attached to a gantry 106 or other mechanical support. One or more chassis motors (not shown) may rotate the gantry 106 and the radiation therapy output 104 around couch 116 when couch 116 is inserted into the treatment area. In an embodiment, gantry 106 may be continuously rotatable around couch 116 when the couch 116 is inserted into the treatment area. In another embodiment, gantry 106 may rotate to a predetermined position when the couch 116 is inserted into the treatment area. For example, the gantry 106 can be configured to rotate the therapy output 104 around an axis ("A"). Both the couch 116 and the radiation therapy output 104 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 116 movements or rotations in order to properly position the patient in or out of the radiation beam 108 position according to a radiation therapy treatment plan. As both the couch 116 and the gantry 106 are independently moveable from one another in multiple degrees of freedom, which allows the patient to be positioned such that the radiation beam 108 precisely can target the tumor.

The coordinate system (including axes A, T, and L) shown in FIG. 1B can have an origin located at an isocenter 110. The isocenter can be defined as a location where the radiation therapy beam 108 intersects the origin of a coordinate axis, such as to deliver a prescribed radiation dose to a location on or within a patient. For example, the isocenter 110 can be defined as a location where the radiation therapy beam 108 intersects the patient for various rotational positions of the radiation therapy output 104 as positioned by the gantry 106 around the axis A.

Gantry 106 may also have an attached imaging detector 114. The imaging detector 114 preferably located opposite to the radiation source 104, and in an example, the imaging detector 114 can be located within a field of the therapy beam 108.

The imaging detector 114 can be mounted on the gantry 106 preferably opposite the radiation therapy output 104, such as to maintain alignment with the therapy beam 108. The imaging detector 114 rotating about the rotational axis as the gantry 106 rotates. In an embodiment, the imaging detector 114 can be a flat panel detector (e.g., a direct detector or a scintillator detector). In this manner, the imaging detector 114 can be used to monitor the therapy beam 108 or the imaging detector 114 can be used for imaging the patient's anatomy, such as portal imaging. The control circuitry of radiotherapy device 102 may be integrated within system 100 or remote from it, and is functionally represented by image processing device 12 as shown in FIG. 1A.

In an illustrative example, one or more of the couch 116, the therapy output 104, or the gantry 106 can be automatically positioned, and the therapy output 104 can establish the therapy beam 108 according to a specified dose for a particular therapy delivery instance. A sequence of therapy deliveries can be specified according to a radiation therapy treatment plan, such as using one or more different orientations or locations of the gantry 106, couch 116, or therapy output 104. The therapy deliveries can occur sequentially, but can intersect in a desired therapy locus on or within the patient, such as at the isocenter 110. A prescribed cumulative dose of radiation therapy can thereby be delivered to the therapy locus while damage to tissue nearby the therapy locus is reduced or avoided.

Figure 1C:
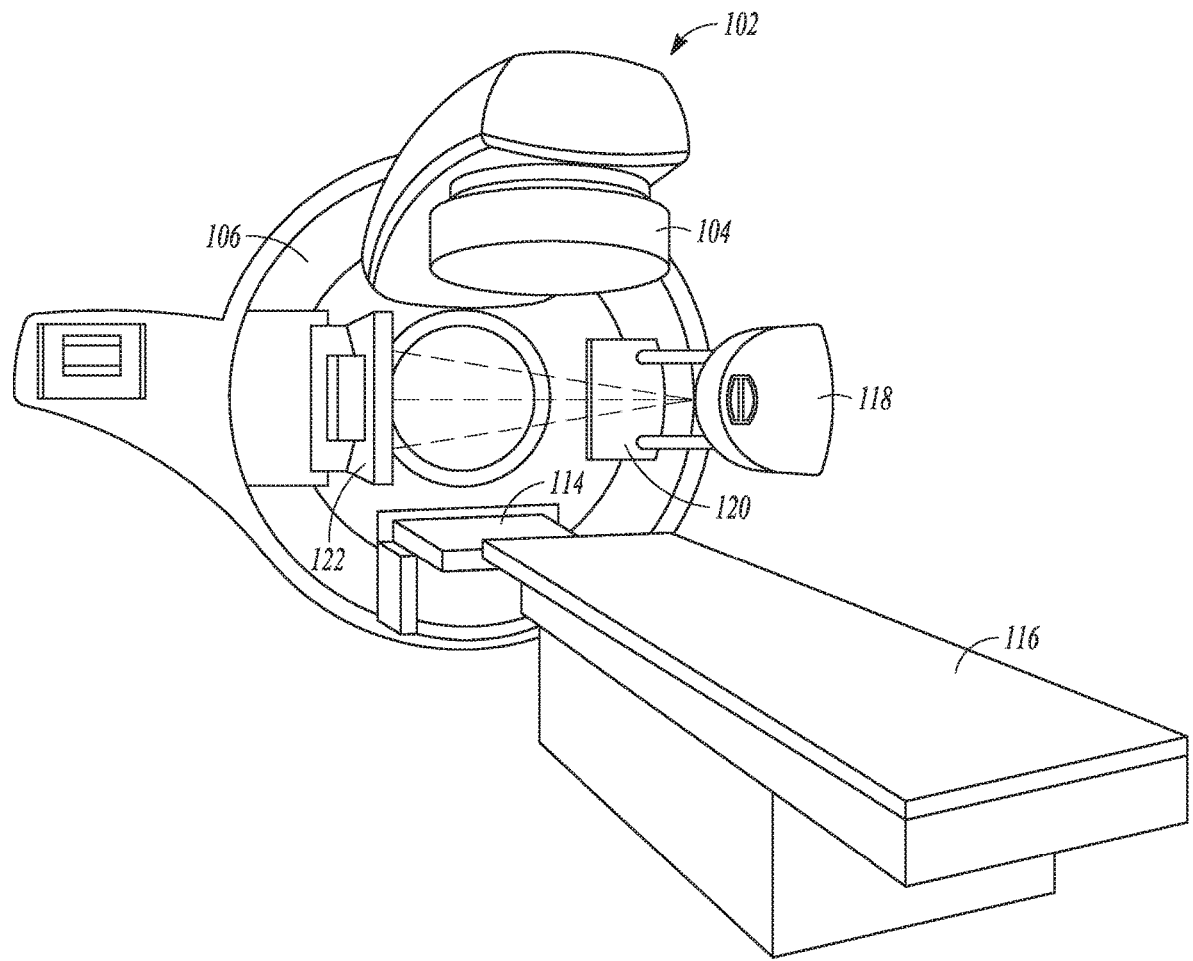
FIG. 1C illustrates an exemplary system including a combined radiation therapy system and an imaging system, such as a computed tomography (CT) imaging system.

FIG. 1C illustrates an exemplary radiation therapy device 102 that may include combining a linear accelerator and an imaging system, such as a computed tomography (CT) imaging system. The CT imaging system can include an imaging X-ray source 118, such as providing X-ray energy in a kiloelectron-Volt (keV) energy range. The imaging X-ray source 118 provides a fan-shaped and/or a conical beam 120 directed to an imaging detector 122, such as a flat panel detector. The radiation therapy system 102 can be similar to the system 102 described in relation to FIG. 1B, such as including a radiation therapy output 104, a gantry 106, a platform 116, and another flat panel detector 114. The X-ray source 118 can provide a comparatively-lower-energy X-ray diagnostic beam, for imaging.

In the illustrative example of FIG. 1C, the radiation therapy output 104 and the X-ray source 118 can be mounted on the same rotating gantry 106, rotationally-separated from each other by 90 degrees. In another example, two or more X-ray sources can be mounted along the circumference of the gantry 106, such as each having its own detector arrangement to provide multiple angles of diagnostic imaging concurrently. Similarly, multiple radiation therapy outputs 104 can be provided.

Figure 1D:
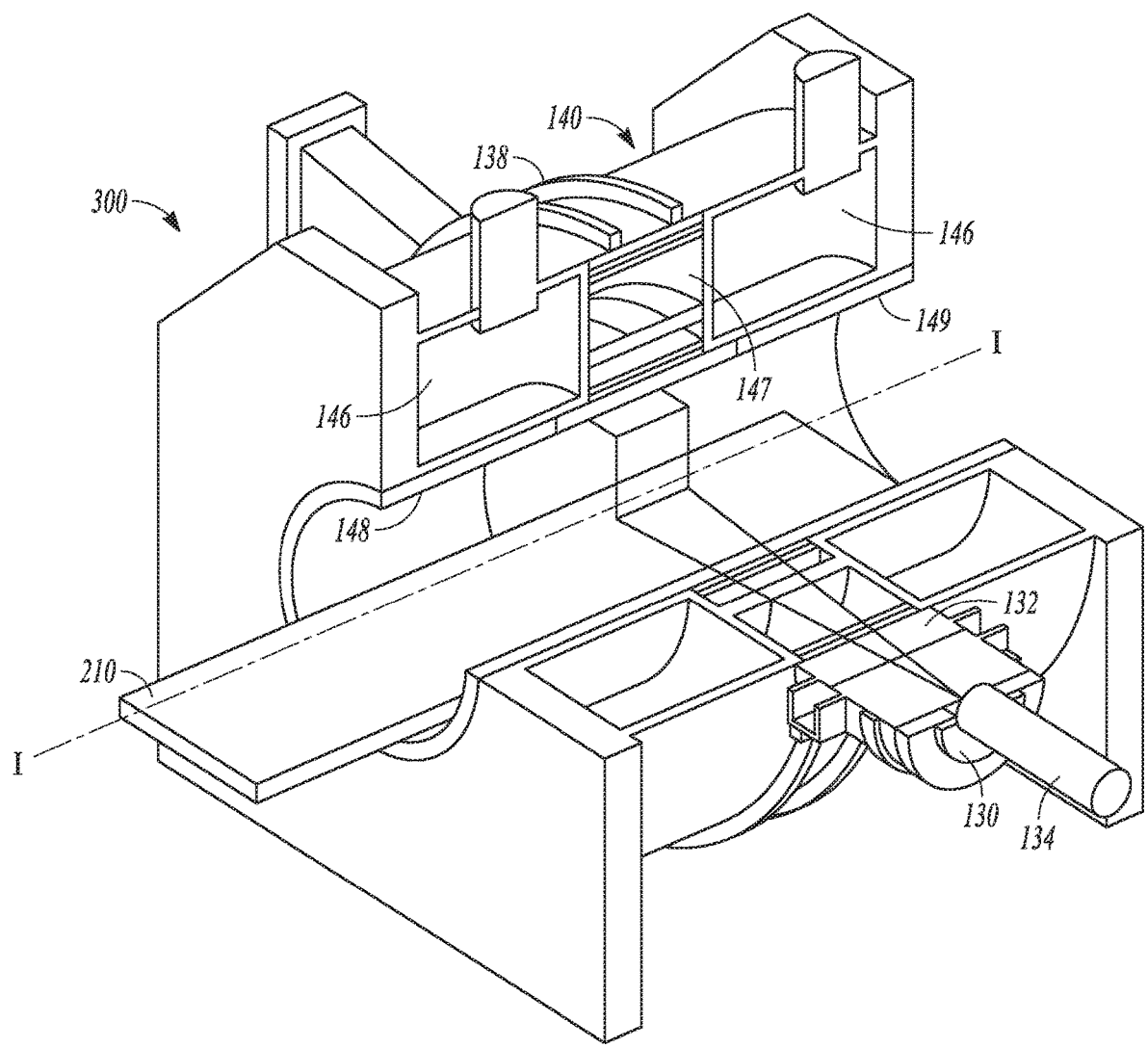
FIG. 1D illustrates a partially cut-away view of an exemplary system including a combined radiation therapy system and an imaging system, such as a nuclear magnetic resonance (MR) imaging system.

FIG. 1D depicts an exemplary radiation therapy system 300 that can include combining a radiation therapy device and an imaging system, such as a nuclear magnetic resonance (MR) imaging system (e.g., known in the art as an MR-Linac) consistent with the disclosed embodiments. As shown, system 300 may include a couch 210, an image acquisition device 140, and a radiation delivery device 130. System 300 delivers radiation therapy to a patient in accordance with a radiotherapy treatment plan. In some embodiments, image acquisition device 140 may correspond to image acquisition device 32 in FIG. 1A that may acquire origin images of a first modality (e.g., MRI image shown in FIG. 4A) or destination images of a second modality (e.g., CT image shown in FIG. 4B).

Couch 210 may support a patient (not shown) during a treatment session. In some implementations, couch 210 may move along a horizontal, translation axis (labelled "I"), such that couch 210 can move the patient resting on couch 210 into and/or out of system 300. Couch 210 may also rotate around a central vertical axis of rotation, transverse to the translation axis. To allow such movement or rotation, couch 210 may have motors (not shown) enabling the couch to move in various directions and to rotate along various axes. A controller (not shown) may control these movements or rotations in order to properly position the patient according to a treatment plan.

In some embodiments, image acquisition device 140 may include an MRI machine used to acquire 2D or 3D MRI images of the patient before, during, and/or after a treatment session. Image acquisition device 140 may include a magnet 146 for generating a primary magnetic field for magnetic resonance imaging. The magnetic field lines generated by operation of magnet 146 may run substantially parallel to the central translation axis I. Magnet 146 may include one or more coils with an axis that runs parallel to the translation axis I. In some embodiments, the one or more coils in magnet 146 may be spaced such that a central window 147 of magnet 146 is free of coils. In other embodiments, the coils in magnet 146 may be thin enough or of a reduced density such that they are substantially transparent to radiation of the wavelength generated by radiotherapy device 130. Image acquisition device 140 may also include one or more shielding coils, which may generate a magnetic field outside magnet 146 of approximately equal magnitude and opposite polarity in order to cancel or reduce any magnetic field outside of magnet 146. As described below, radiation source 134 of radiotherapy device 130 may be positioned in the region where the magnetic field is cancelled, at least to a first order, or reduced.

Image acquisition device 140 may also include two gradient coils 148 and 149, which may generate a gradient magnetic field that is superposed on the primary magnetic field. Gradient coils 148 and 149 may generate a gradient in the resultant magnetic field that allows spatial encoding of the protons so that their position can be determined. Gradient coils 148 and 149 may be positioned around a common central axis with the magnet 146, and may be displaced along that central axis. The displacement may create a gap, or window, between coils 148 and 149. In the embodiments wherein magnet 146 also includes a central window 147 between coils, the two windows may be aligned with each other.

In some embodiments, image acquisition device 140 may be an imaging device other than an MRI, such as an X-ray, a CT, a CBCT, a spiral CT, a PET, a SPECT, an optical tomography, a fluorescence imaging, ultrasound imaging, or radiotherapy portal imaging device, etc. As would be recognized by one of ordinary skill in the art, the above description of image acquisition device 140 concerns certain embodiments and is not intended to be limiting.

Radiotherapy device 130 may include the source of radiation 134, such as an X-ray source or a linear accelerator, and a multi-leaf collimator (MLC) 132 (shown below in FIG. 2). Radiotherapy device 130 may be mounted on a chassis 138. One or more chassis motors (not shown) may rotate chassis 138 around couch 210 when couch 210 is inserted into the treatment area. In an embodiment, chassis 138 may be continuously rotatable around couch 210, when couch 210 is inserted into the treatment area. Chassis 138 may also have an attached radiation detector (not shown), preferably located opposite to radiation source 134 and with the rotational axis of chassis 138 positioned between radiation source 134 and the detector. Further, radiation therapy system 300 may include control circuitry (not shown) used to control, for example, one or more of couch 210, image acquisition device 140, and radiotherapy device 130. The control circuitry of radiotherapy device 130 may be integrated within the radiation therapy system 300 or remote from it.

During a radiotherapy treatment session, a patient may be positioned on couch 210. System 300 may then move couch 210 into the treatment area defined by magnetic coils 146, 148, 149, and chassis 138. Control circuitry may then control radiation source 134, MLC 132, and the chassis motor(s) to deliver radiation to the patient through the window between coils 148 and 149 according to a radiotherapy treatment plan.

FIG. 1B, FIG. 1C, and FIG. 1D generally illustrate examples of radiation therapy devices configured to provide radiotherapy treatment to a patient, including configurations where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient.

As discussed above, radiation therapy devices described by FIG. 1B, FIG. 1C, and FIG. 1D include a multi-leaf collimator for shaping, directing, or modulating an intensity of a radiation therapy beam to the specified target locus within the patient. FIG. 2 illustrates an exemplary multi-leaf collimator (MLC) 132 that includes leaves 132A through 132J that can be automatically positioned to define an aperture approximating a tumor 140 cross section or projection. The leaves 132A through 132J permit modulation of the radiation therapy beam. The leaves 132A through 132J can be made of a material specified to attenuate or block the radiation beam in regions other than the aperture, in accordance with the radiation treatment plan. For example, the leaves 132A through 132J can include metallic plates, such as comprising tungsten, with a long axis of the plates oriented parallel to a beam direction, and having ends oriented orthogonally to the beam direction (as shown in the plane of the illustration of FIG. 1B). A "state" of the MLC 132 can be adjusted adaptively during a course of radiation therapy treatment, such as to establish a therapy beam that better approximates a shape or location of the tumor 140 or other target locus. This is in comparison to using a static collimator configuration or as compared to using an MLC 132 configuration determined exclusively using an "offline" therapy planning technique. A radiation therapy technique using the MLC 132 to produce a specified radiation dose distribution to a tumor or to specific areas within a tumor can be referred to as Intensity Modulated Radiation Therapy (IMRT).

Figure 3:
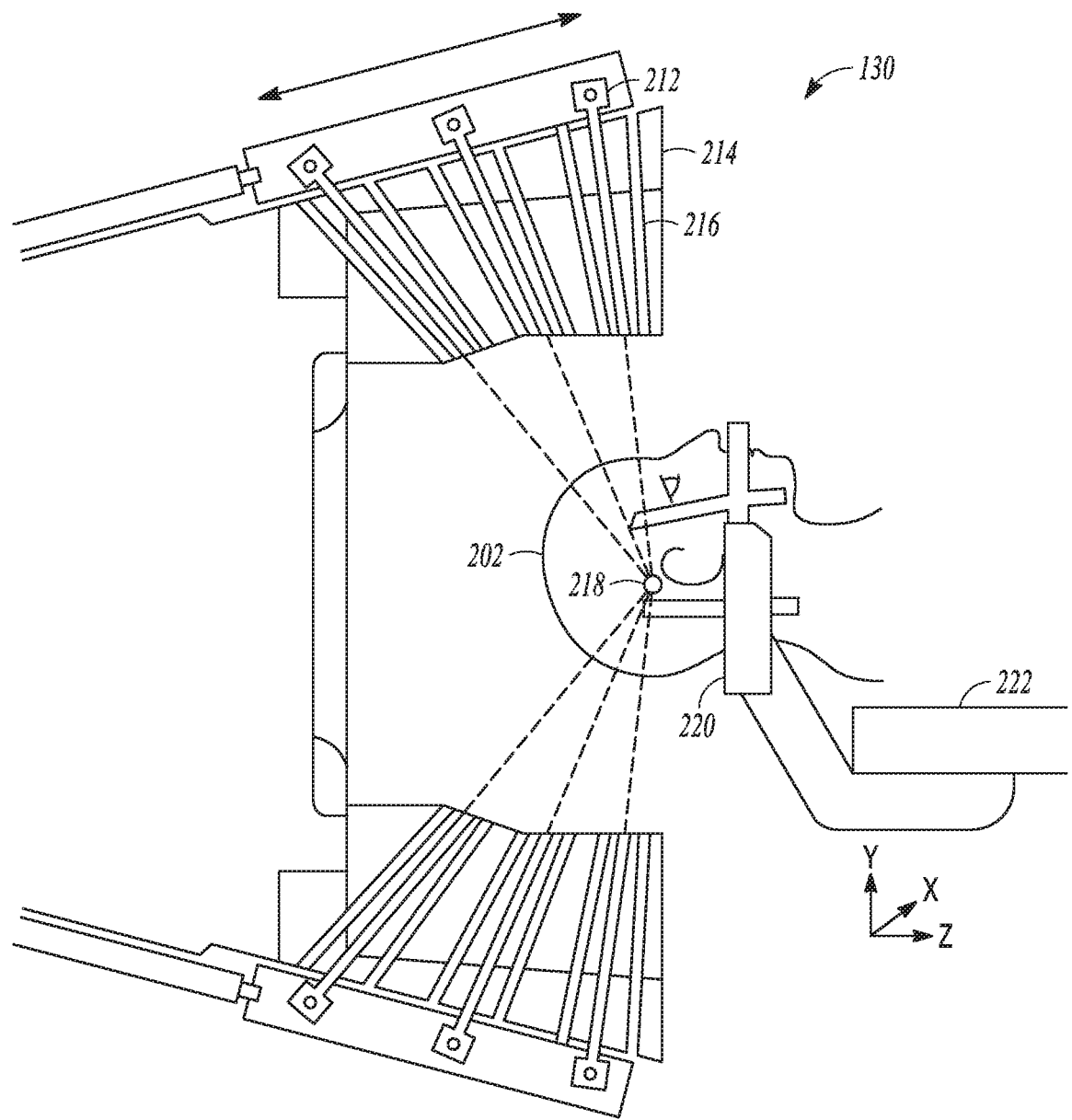
FIG. 3 illustrates an exemplary Gamma knife radiation therapy system.

FIG. 3 illustrates an example of another type of radiotherapy device 130 (e.g., a Leksell Gamma Knife), according to some embodiments of the present disclosure. As shown in FIG. 3, in a radiotherapy treatment session, a patient 202 may wear a coordinate frame 220 to keep stable the patient's body part (e.g., the head) undergoing surgery or radiotherapy. Coordinate frame 220 and a patient positioning system 222 may establish a spatial coordinate system, which may be used while imaging a patient or during radiation surgery. Radiotherapy device 130 may include a protective housing 214 to enclose a plurality of radiation sources 212. Radiation sources 212 may generate a plurality of radiation beams (e.g., beamlets) through beam channels 216. The plurality of radiation beams may be configured to focus on an isocenter 218 from different directions. While each individual radiation beam may have a relatively low intensity, isocenter 218 may receive a relatively high level of radiation when multiple doses from different radiation beams accumulate at isocenter 218. In certain embodiments, isocenter 218 may correspond to a target under surgery or treatment, such as a tumor.

FIGS. 4A and 4B depict the differences between exemplary images acquired using different imaging modalities, based on which image acquisition device 32 is utilized. For example, different image modalities characterize patient tissue differently. As a result, images acquired of the same underlying object using different image modalities often may not resemble each other in image characteristics. For example, FIG. 4A shows a two-dimensional (2D) image of a patient's head acquired using an MRI device to acquire the image; and FIG. 4B, shows a corresponding 2D image of the same object acquired using a CT device. As shown in FIGS. 4A and 4B, the two images represent the same object, but they present noticeably different image characteristics. For example, in FIG. 4A, the skull and vitreous body have roughly identical intensity values as shown by the MRI image. However, in contrast, FIG. 4B depicts very different intensity values for the skull and vitreous body as indicated by the brightness (e.g., white outline) of the skull as shown by the CT image. Therefore, the MRI image and the CT image intensity values can greatly differ.

The disclosed systems and methods are directed to generating a synthetic image (e.g., pseudo-CT image) from an origin image acquired using a first modality (e.g., an MRI image as exemplary shown in FIG. 4A) to resemble a destination image (e.g., a CT image as exemplary shown in FIG. 4B) acquired using a second modality.

Figure 4C:
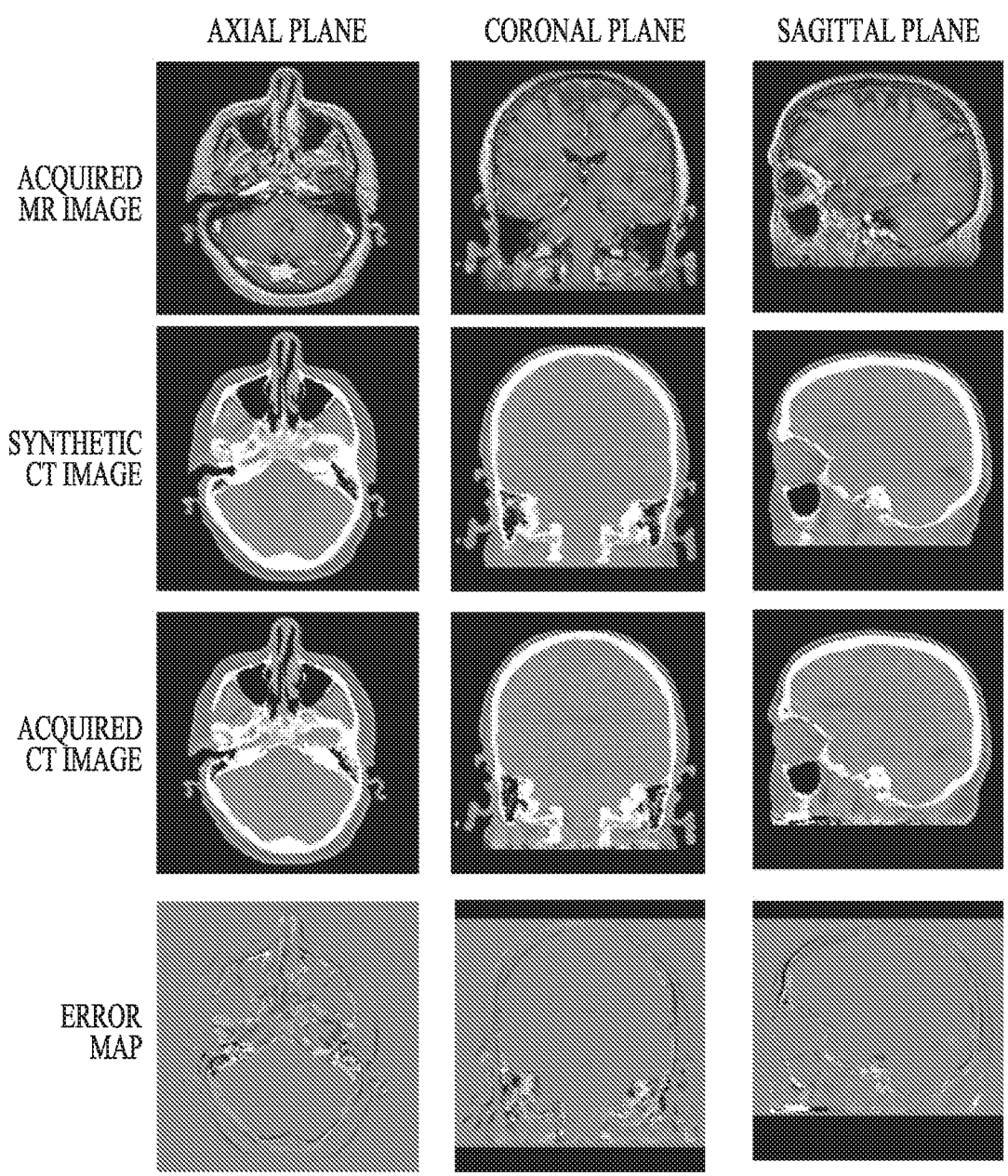
FIG. 4C depicts exemplary synthetic CT images generated from acquired MRI images.

Referring to FIG. 4C, which compares MR and CT images of a patient's head from three different planes and provides an error map. For example, the top row of FIG. 4C depicts three origin images acquired using MRI from three different anatomical planes. The second row depicts synthetic CT images, generated based on the MRI images shown in the top row, using the disclosed image conversion systems and methods. The third row depicts three-planar images of the same object acquired using CT. The fourth row shows error maps representing the differences between the synthetic CT images (second row) and the acquired CT images (third row). As shown in the fourth row, the synthetic CT images provide pixel values closely resembling the CT values in the acquired CT images for most parts of the head region. In the example of FIG. 4C, the error maps indicate that errors (e.g., differences in intensity between corresponding voxels in a synthetic CT image and a corresponding real CT image) are minimal (e.g., within a noise level of a typical CT image) and restricted to interfaces between different tissue types, especially around the borders of bones and air.

Figure 5:
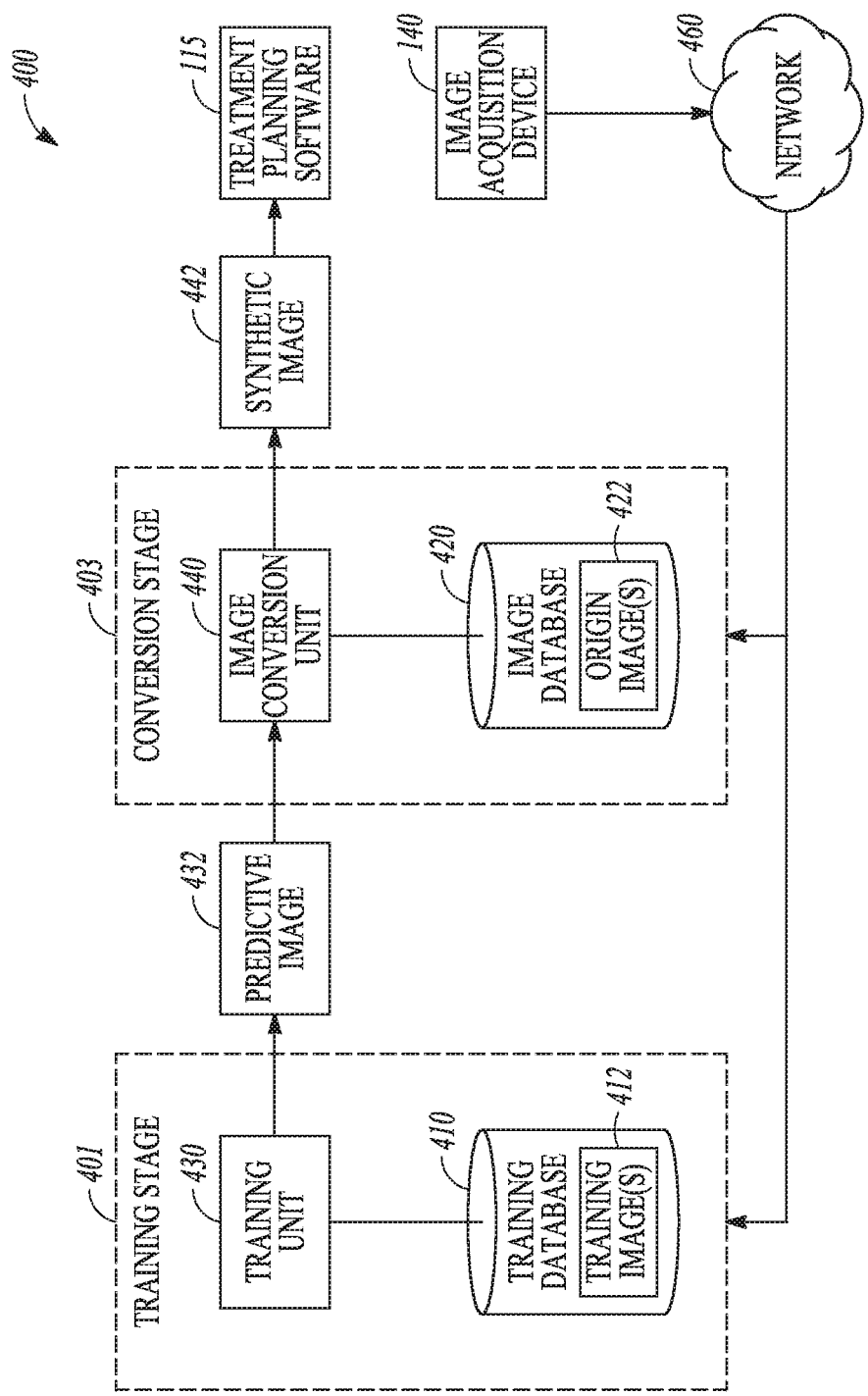
FIG. 5 depicts an exemplary image conversion system, according to some embodiments of the present disclosure.

FIG. 5 depicts an exemplary image conversion system 400, consistent with disclosed embodiments. In some embodiments, image conversion system 400 may include an image acquisition device 140, an image database 420, an image conversion unit 440, a training database 410 storing training images 412, a training unit 430, and a network 460. The imaging conversion system 400 can perform two functions: (a) provide a training unit 430 to train a predictive model using the training images 412; (b) provide an image conversion unit 440 configured to use the trained predictive model to generate synthetic images. In an example, the image acquisition device 140 can correspond to the image acquisition device 32 as shown in FIG. 1A.

The disclosed systems and methods use predictive models to generate synthetic images. Consistent with the above disclosure, the term "synthetic image," as used herein, generally refers to any computer-generated image data representing or resembling an image acquired in one modality (e.g., a CT image), while based on actual image data acquired from an imaging device using a different modality (e.g., an MRI image). As explained below, such synthetic images are converted from origin images acquired using a first modality (e.g., MRI) to resemble images generated using a second modality (e.g., CT). The predictive model may advantageously enable automatic conversion of images without the need for tissue classification, registration to an atlas, or model-based methods that require manually crafted features.

In some embodiments, the disclosed systems, methods, devices, and processes concern generation of synthetic CT images from images acquired using another modality, such as MRI images. In some aspects, the predictive models may be neural networks, such as types of convolutional neural networks (CNN) or deep neural networks, and other types of artificial intelligence known in the art. Synthetic image generation may thus include two stages. In a first stage, the predictive model may be generated (also known as "trained" or "learned") using training data, including training MRI images and their corresponding real CT images. The training process may automatically use the training data to learn parameters or weights of the predictive model. These parameters or weights may be learned iteratively, according to an optimality criterion. In a second stage, synthetic CT images (e.g., also referred to as pseudo-CT images) may be generated from the MRI images using the predictive model.

An "origin image" may refer to an image acquired using a first imaging modality, such as nuclear magnetic resonance imaging (MRI). A "destination image" may refer to an image acquired using a second modality differing from the first modality, such as computed tomography (CT).

As described above, a "synthetic image" may refer to an image generated from one or more "origin images," but resembling a "destination image." In some embodiments, the synthetic image may be referred to as a pseudo-CT image. That is, the synthetic image may have the characteristics of the destination image. For example, a synthetic CT image ("synthetic image") generated from one or more MRI images ("origin images") may have the characteristics of a real CT image that is acquired by a CT scanner ("destination image"). Throughout this disclosure, examples will be discussed as the origin image being a MRI image and the destination image being a CT image. But this is not a limitation. Alternatively, for example, the origin image could be a CT image and the destination image be a MRI image. In an example where a synthetic CT image can be generated from one or more MRI images, the synthetic CT image can be used in a radiotherapy planning process, without exposing a patient to ionizing radiation as in a typical CT imaging process.

As used herein, an image "resembles" another image when a difference between the two images is smaller than predetermined threshold criteria. In an example, a synthetic CT image can "resemble" a corresponding CT image if voxel by voxel differences in intensity between the two images are less than 20 Hounsfield units, and in some examples, less than 100 Hounsfield units in average. For example, the difference may be determined as an error map indicating the differences in pixel values between the two images. The difference may be measured by a loss function, such as a mean absolute error or a mean squared error calculated based on the two images. However, synthetic images (e.g., pseudo-CT images) consistent with the present disclosure may be shown to resemble a destination image using other types of image threshold criteria. Further, systems and methods consistent with the present disclosure do not necessarily need to apply any such predetermined threshold criteria in order for a destination image to resemble an origin image. In other words, and as described below, systems and methods consistent with this disclosure may use any such predetermined threshold criteria to potentially validate a degree of resemblance between the origin and destination images. The systems and methods consistent with the present disclosure may generate synthetic images (e.g., including pseudo-CT images) that meets the predetermined threshold criteria.

In order to for the training unit 430 to train a predictive model, training images may be utilized. Training database 410 may be configured to store one or more sets of training images 412, consistent with the disclosed embodiments. Each set of training images may include one or more origin images ("origin images") acquired using the first imaging modality and corresponding destination images ("destination images") acquired in the second imaging modality. The one or more origin images and the corresponding destination images are acquired of the same object, and may include corresponding views of this object (e.g., images of the same anatomical portion taken at substantially the same orientation, but using different types of image modalities). As explained below, the origin images and destination images may be either 2D or 3D images. In some embodiments, database 410 may be part of an oncology information system that manages oncology treatment plans for patients. In some aspects, database 410 may receive these image sets from an image database having images previously acquired by image acquisition device 140 during one or more radiotherapy treatment sessions.

Image database 420 may store images acquired using the first imaging modality. In some embodiments, image acquisition device 140 may acquire the images stored in image database 420. The images stored in image database 420 may also correspond to images acquired during one or more radiotherapy treatment sessions. As explained below, the images may be 2D and/or 3D images.

In some aspects, image conversion system 400 may be configured to perform a training stage. In some embodiments, training unit 430 may be configured to use training data from training database 410 to train a predictive model. Training unit 430 may be implemented in hardware and/or software, as would be recognized by one of skill in the art. During the training stage, training unit 430 may be configured to generate estimated synthetic images based on training origin images received from training database 410. Training unit 430 may also generate error maps by comparing the estimated synthetic images to training destination images (e.g., CT images) and may then adjust the parameters of the predictive model based on the generated error maps that identify differences between the synthetic images and the real CT images. Training unit 430 may be configured to continue training the predictive model until certain stopping criteria are satisfied (check error between model prediction and real CT image, can also be trained based on number of iterations of training, or if model error is less than a threshold value). In an example, the stopping criteria can be satisfied when a number of training iterations exceeds a threshold value (e.g., when there have been more than 100 training epochs—in neural network training, one epoch can be equal to the number of iterations to go through all training data one time) In an example, the stopping criteria can be satisfied if a voxel by voxel difference in intensity between the two images is less than a threshold value (e.g., 20 Hounsfield unit). Training unit 430 may then save the trained predictive model, which may later be used by image conversion unit 440.

In another aspect, the image conversion system 400 may also be configured to perform a conversion stage. During the conversion stage, image conversion unit 440 may be configured to receive a trained predictive model from training unit 430. In some embodiments, image conversion unit 440 may be configured to generate synthetic images from origin images 422 received from image database 420. Image conversion unit 440 may be implemented in hardware and/or software, as would be recognized by one of skill in the art. Image conversion unit 440 may be configured to generate the synthetic images using the trained predictive model and the received origin images 422.

In some embodiments, image conversion system 400 may be configured to display the synthetic image to be accessed by a user interface e.g., a graphical user interface as provided with a computer which may also include a tablet, an iPad, a mobile device and the like), store the synthetic image in image database 420 for further use in treatment planning, and provide the synthetic image to Treatment Planning Software 115. As an additional example, image conversion system 400 may be configured to store the origin image and the synthetic image in training database 410. Such stored images may become part of training images 412. In various aspects, storage of the origin image and the synthetic image may be automatic, semi-automatic, or manual. Image conversion unit 440 may be implemented in hardware and/or software, as would be recognized by one of skill in the art.

Image acquisition device 140, as discussed with regard to FIG. 1, may be configured to acquire images using one or more imaging modalities (as described above), including MRI, functional MRI (e.g., fMRI, DCE-MRI and diffusion MRI), CT, CBCT, spiral CT, PET, SPECT, X-ray, optical tomography, fluorescence imaging, ultrasound imaging, and radiotherapy portal imaging, etc. In some embodiments, image acquisition device 140 may provide acquired images to training database 410, image database 420, training unit 430, and image conversion unit 440.

Network 460 may be configured to provide communications between the components of FIG. 4. For example, network 460 may be any type of network (including infrastructure) that provides communications, exchanges information, and/or facilitates the exchange of electronic information between one or more devices. In this regard, network 460 may include a wired connection (e.g., a LAN or other hardwired connection), a wireless connection (e.g., WiFi, Bluetooth, ZigBee, NFC, WiMAX, LET and the like), a computer bus, a serial connection, a parallel connection, an Ethernet connection, a local area network or a wide area network, an internet connection, a satellite connection, or any other suitable connection(s), including a connection to a cloud computing service, or any combination thereof that enables the components of image conversion system 400 to send and to receive information between each other in any format and under any communications protocol.

It is contemplated that FIG. 4 illustrates only an exemplary arrangement of image conversion system 400. In some embodiments, additional components may be added, and/or the depicted components may be combined, divided, modified, or removed. For example, the training stage may be performed in advance and performed separately by another system. Accordingly, image conversion system 400 may not include training database 410 or training unit 430. Further, in some aspects, at least one component of image conversion system 400 may be located geographically remotely from the remaining components, and may communicate with the remaining components through the network 460. For example, the training stage including the training unit 430 and training database 410 may be located in the research and development department; whereas the conversion stage including the image conversion unit and origin images may be located in the radiotherapy clinic.

In still other embodiments, two or more components of image conversion system 400 may be implemented at a single location (e.g., a radiotherapy treatment room). Also, while FIG. 4 shows various components of image conversion system 400 as separate, image conversion system 400 may implement some of these components in a single device. For example, database 410 and training unit 430 may be implemented within a single device, such as a tablet, a laptop, a desktop, a workstation, a server, or a purpose-built image conversion device. Similarly, training unit 430 and image conversion unit 440 may be implemented within a single device.

Figure 6:
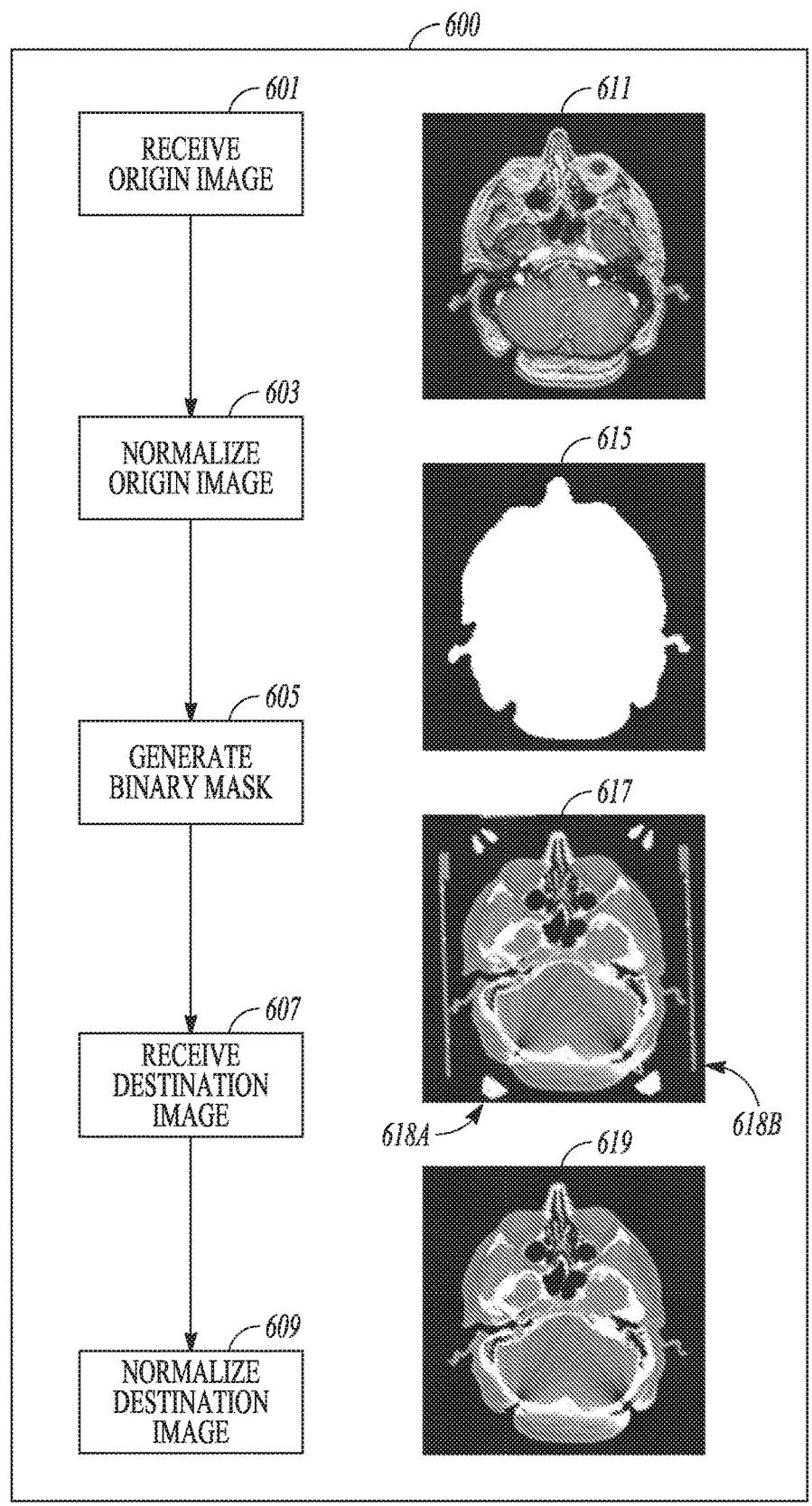
FIG. 6 illustrates an exemplary image pre-processing process, according to some embodiments of the present disclosure.

FIG. 6 illustrates an exemplary image pre-processing process 600. Process 600 may be performed by training unit 430 as part of the training stage or prior to processing done by the training stage. Certain aspect of process 600, (e.g., receiving the origin image 601) may also be performed by image conversion unit 440 as part of or prior to the conversion stage. At 601, image conversion system 400 may receive an origin image 422 of a patient that was acquired using a first imaging modality. Consistent with the disclosed embodiments, the origin image 422 may be received from an image acquisition device 140, or alternatively, the image conversion system 400 may receive a training image 412 from training database 410. The image conversion system then provides the origin image to be normalized.

At 603, training unit 430 may normalize the origin image 422. This normalization process may improve the accuracy of image conversion system 400 by standardizing the input image data provided to the predictive model. Here, at 603, the training unit 430 may perform a variety of processing functions on the origin image 422 to generate a normalized origin image with a standardized alignment, resolution, and/or intensity value distribution. For example, training unit 430 may align the acquired origin image 422 with a standard CT image such as to adjust the orientation of the object in the image. Training unit 430 may also resample the origin image 422 so that the normalized origin image has a reference resolution and/or reference field of view. For example, the origin image may be up-sampled using interpolation methods or down-sampled using averaging or max pooling methods. In an example, the origin image can be up-sampled or down-sampled, such as to provide an origin image having the same spatial resolution as a corresponding destination image.

Further, the training unit 430 may correct the intensity value distribution of the origin image 422 to better approximate a standardized intensity value distribution. For example, when the origin image 422 is an MRI image (e.g., exemplary image 611), training unit 430 may use the N3 bias field correction algorithm known in the art to correct intensity non-uniformities in the origin image. As known in the art, other correction algorithms may be applied, such as joint histogram registration, landmarks or histogram matching, or dynamic histogram warping. At the end of 603, a normalized origin image is created and provided to 605.

At 605, training unit 230 may generate a binary mask (e.g., exemplary image 615) from the normalized origin image. The training unit 430 may be configured to use the binary mask to remove undesirable portions (e.g., corresponding to a stereotactic head frame) of the normalized origin image 422. The training unit 430 may generate the binary mask by applying thresholding and spatially filtering to the normalized origin image. The training unit 430 may automatically determine the thresholds based on a histogram of image intensity values of the origin image 422, according to methods known to one of skill in the art. For example, training unit 430 may determine a threshold value to apply or compare to each intensity value of the normalized origin image. The training unit 430 may compare each intensity value of the normalized origin image with a threshold value. The predetermined threshold value may be a default intensity value. Through this comparison, the training unit 430 may produce a binary mask image having logical "1" or "0" intensity values. The intensity values in the binary mask image depend on whether the corresponding intensity values of the original origin image meet or exceed the threshold value. In some implementations, training unit 430 may also spatially filter this resulting binary mask image using known morphological operations to generate the final binary mask.

The training unit 430 may then use the generated binary mask to remove the stereotactic head frame in an origin image. For example, portions of the origin image within the binary mask may keep their original intensity values. Other portions of the destination image outside the binary mask may then be set to a predetermined intensity value.

At 607, training unit 430 may receive a destination image 412 of the same object acquired using another imaging modality (e.g., CT image 617). The destination image 412 can be received from the training database 410. This destination image 412 may correspond to the object(s) shown in the origin image 611. For example, the origin image 611 may be an MRI image of a particular portion of a patient's anatomy and the destination image 412 may be a corresponding CT image of the same anatomical portion. Training unit 430 may receive the destination image 412 from image acquisition device 140 or training database 410. For example, when the destination image 412 is a CT image, the destination image 412 may include portions of a stereotactic head frame (e.g., image element 618a and image element 618b that correspond to the head frame). Typically, the stereotactic head frame is not shown in the corresponding MRI image (e.g., the origin image 611).

At 609, training unit 430 may normalize the destination image 412. The normalization of the origin image 611 was described above, here, at 609, normalization of the destination image may improve the accuracy of image conversion system 400. The normalization of the destination image is performed by standardizing the input data provided to train the predictive model, e.g., neural network 700, as shown in FIG. 7D, described below. The training unit 430 may perform a variety of processing functions on the destination image to generate a normalized destination image with a standardized alignment, resolution, and/or intensity value distribution.

In some aspects, an image registration or image alignment process is performed to align the destination image with the origin image for each pair of training images. This is needed because the destination and the origin images may be acquired by different imaging devices or at different scanning times, and hence they may not be spatially aligned.

In some aspects, the destination image may also be segmented using the binary mask. For example, the binary mask may correspond to image portions associated with the patient. Other portions of the destination image outside the binary mask may then be set to a predetermined intensity value. The predetermined value may be a default intensity value. For example, when the destination image is a CT image, the portions may be set to a Hounsfield scale value of −1000. In this manner, by using the binary mask, the portion of the CT image showing, for example, the stereotactic head frame may be eliminated or reduced, in whole or in part (e.g., image 619) because the head frame portion was outside the binary mask.

It should be noted, however, that image conversion system 400 may include process 600 as an optional step. In some embodiments, image conversion system 400 not utilize every aspect of process 600. For instance, image conversion system 400 may train the predictive model directly using acquired images. For example, if the images do not contain image features such as the head frame, then process 600 may not be utilized. The disclosed method may be able to train the predictive model to be adaptive to training images without preprocessing. For example, image conversion system 400 may still generate high-quality synthetic images using a predictive model trained on training origin and training destination images that were not pre-processed by using functionality included in process 600.

With or without pre-processing, training unit 430 may use the training images (including the training origin images and training destination images) to train the predictive model. Specifically, the predictive model may be a convolutional neural network (CNN), which is a known type of supervised machine learning. A convolutional neural network may include a stack of distinct layers that transform an input into an output. The layers may differ in input size, output size, and the relationship between the input and the output for the layer. Each layer may be connected to one or more upstream and downstream layers in the stack of layers. The performance of a convolutional neural network may thus depend on the number of layers, and the convolutional neural network's complexity may increase as the number of layers increases. A convolutional neural network may be viewed as "deep" if it has more than one stages of non-linear feature transformation, which typically means the number of layers in the network is above a certain number. For example, some convolutional neural networks may include about 10-30 layers, or in some cases more than a few hundred layers. Examples of convolutional neural network models include AlexNet, VGGNet, GoogLeNet, ResNet, etc. These convolutional neural network models were designed for image recognition tasks, and can be used at the encoding part of the full convolutional neural network model in the disclosed embodiments.

Figure 7A:
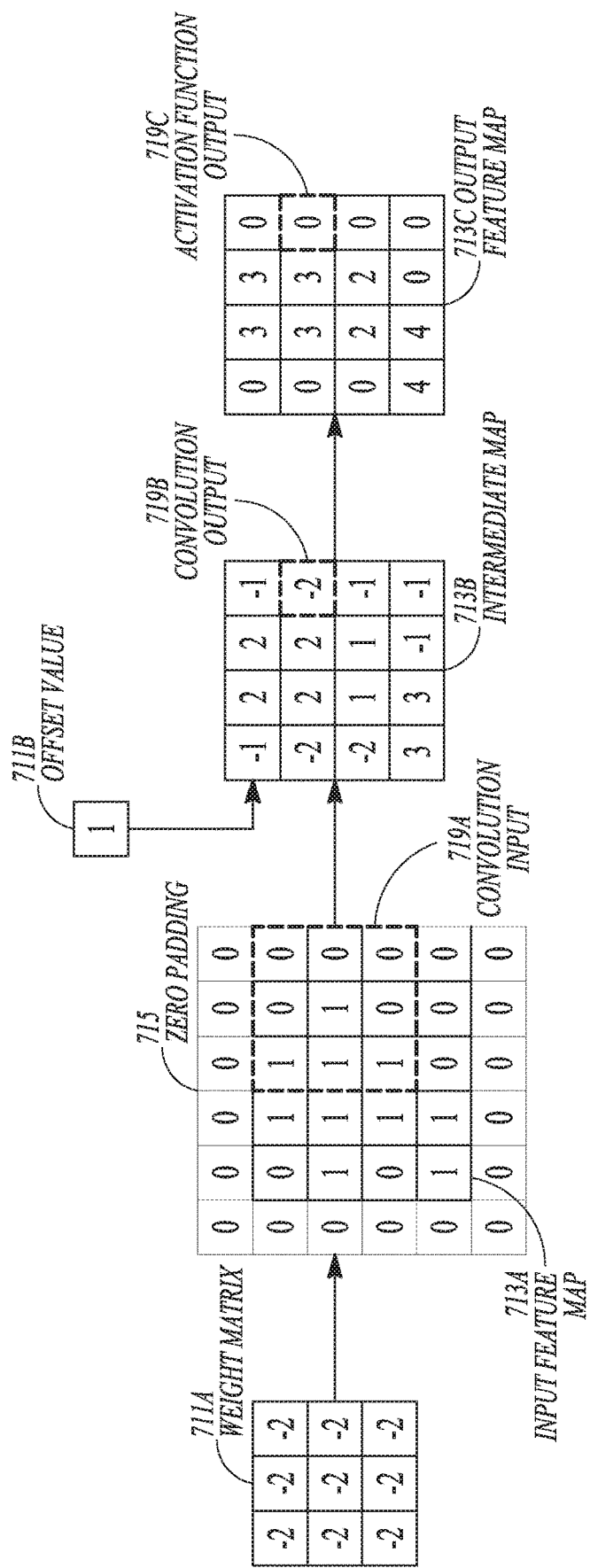
FIG. 7A illustrates the operation of an exemplary convolutional layer of the predictive model shown in FIG. 5, according to some embodiments of the present disclosure.
Figure 7B:
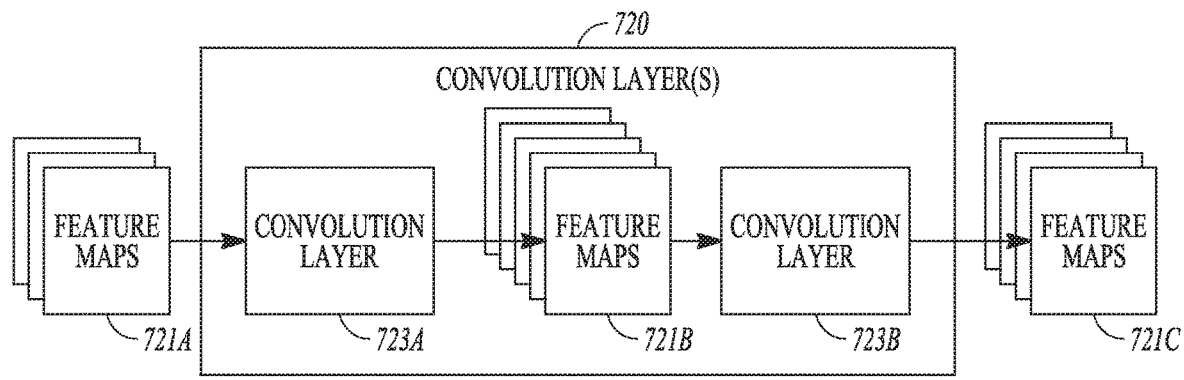
FIG. 7B illustrates the operation of an exemplary stack of convolutional layers of the predictive model shown in FIG. 5, according to some embodiments of the present disclosure.
Figure 7C:
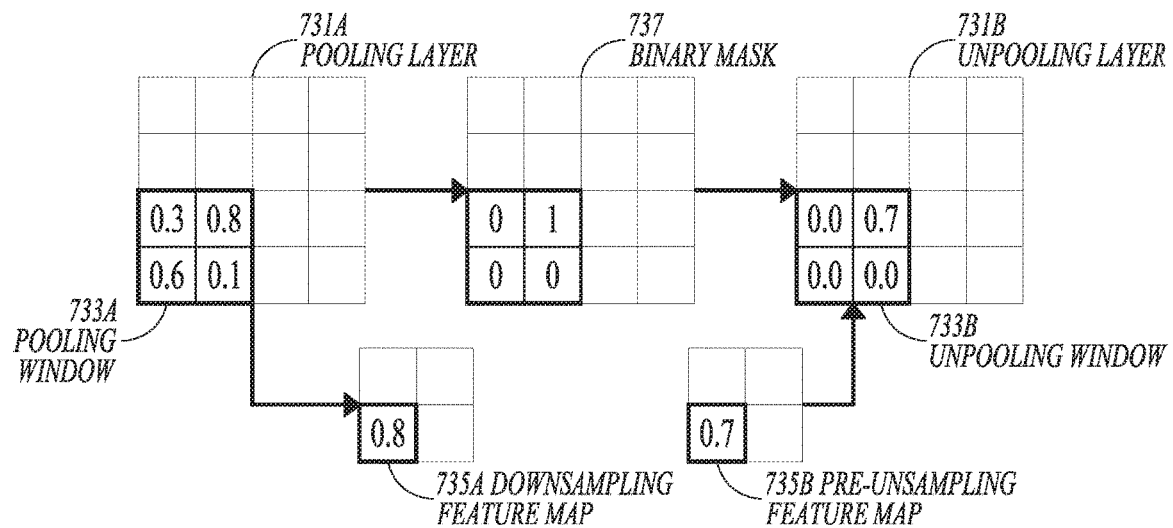
FIG. 7C illustrates the operation of exemplary max pooling and unpooling layers of the predictive model shown in FIG. 5, according to some embodiments of the present disclosure.
Figure 7D:
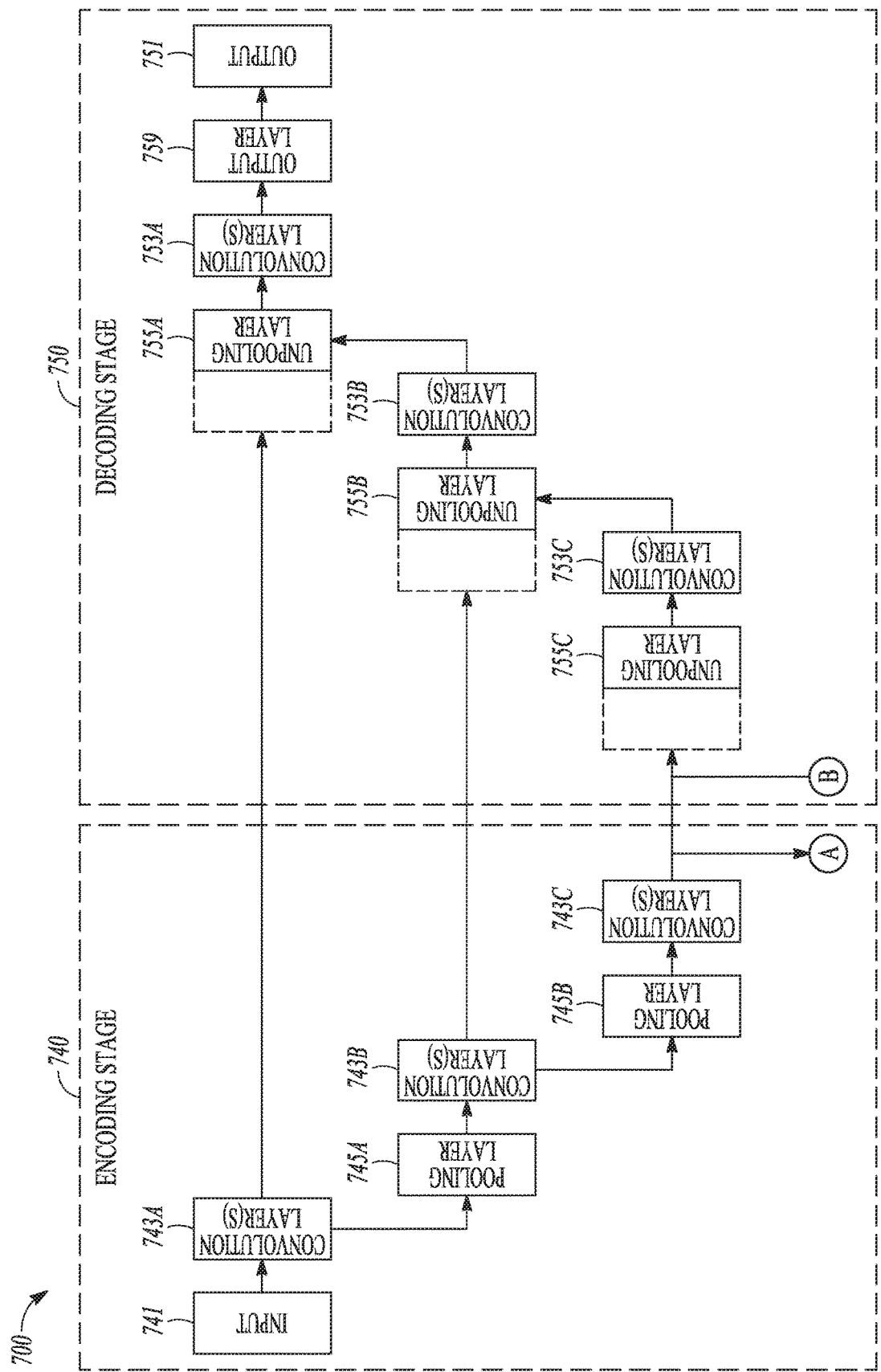

FIGS. 7A-7E illustrate the structure and various components of exemplary convolutional neural network models. Among others, a convolutional neural network may typically include a plurality of convolutional layers, de-convolutional layers, pooling (e.g., down-sampling) layers, and unpooling (e.g., up-sampling) layers. FIG. 7A illustrates the operation of an exemplary convolutional layer of a convolutional neural network. Such a convolutional layer may be configured to perform two- or three-dimensional convolutions of the input to the convolutional layer with a set of learnable filter functions. A learnable filter function may be defined by a matrix of weights W, where each weight is to be applied to an image pixel during a convolution operation, and an offset value b. Weight matrix Wand offset b are among the model parameters that need to be learned during the training stage. The convolutional layer may be configured to further apply an activation function to the result of these convolutions. Non-limiting examples of the activation function include a rectified linear units function, a sigmoid function, a hyperbolic tangent function, or a similar non-linear function. The combination of the filter function and the activation function may be expressed as:

$$h=\max(0, W*X+b) \qquad \text{Eq. 1}$$

Eq. 1 consists of two parts: a learnable filter function W*X+b, and an activation function max(0,•). X may be the input to the filter function W*X+b. In some embodiments, X may be two dimensional (e.g., an image) or three dimensional (e.g. a stack of images). The activation function max(0,•) may be applied to the output of this learnable filter function to generate output h. This output, or feature map, may indicate the importance of features in the input. The activation function max(0,•) may be a rectified linear units function that may act as an activation filter, by zeroing out negative values of the convolution operation. In some embodiments, zero-padding may be used to ensure that the spatial size of h are equivalent to the spatial size of X As a non-limiting example, when X is 1024×1024, zero-padding may be used to ensure that the spatial size of h is also 1024×1024. When a n×n filter function is used, n−1 rows (or columns) of zeros may be added to the margins of matrix X, before X is convoluted with the filter. As a non-limiting example, the learnable filter functions may be 3×3 filters, in which case 2 rows and 2 columns of zeros may be added to X. For example, a row and column of zeros may be added to each margin of X.

To illustrate, FIG. 7A shows the application of a learnable filter function and activation function to a two-dimensional input feature map in a convolutional layer. Here exemplary 3×3 filter function (comprising weight matrix 711a and offset value 711b) and activation function are applied to an exemplary 4×4 input feature map 713a to generate a 4×4 output feature map 713c. Input feature map 713a may be first padded with 2 rows and 2 columns of zeros, as shown by zero padding 715. Here, one column (or row) of zeros may be added to each margin of input feature map 713a. But as would be appreciated by one of skill in the art, the amount of zero padding may depend on the size of weight matrix 711a, and the particular amount and arrangement of zero padding shown is not intended to be limiting. After the zero padding, input feature map 713a becomes 6×6, and may have values $x^{n,m}$ in its nth row, mth column (n, m=1, 2, . . . 6). Weight matrix 711a may contain a total of 9 weights, e.g., $w^{j,k}$ for the weight in the $j^{th}$ row, $k^{th}$ column of the filter matrix. In the example shown, offset value 711b may be a single offset value. The predictive model may be configured to convolve weight matrix 711a with the zero-padded input feature map 713a, the result of which is shown as intermediate map 713b. To perform the convolution, at each position, weight matrix 711a will overlap with a 3×3 portion of the zero-padded input feature map 713a. For example, as shown in FIG. 7A, weight matrix 711a may overlap with the 3×3 portion centered at $x^{3,5}$ (convolution input 719a). The respective pixel values of input feature map 713a may be multiplied with the respective weights overlapping with them, and the multiplication results are summed to derive value $h^{2,4}$ in intermediate map 713*b* (convolution output 719*b*). The convolutional layer may generate output feature map 713*c* by summing each element of intermediate map 713*b* with offset value 711*b* and applying activation function max(0,•) to each resulting sum. For example, as shown in FIG. 7A, when the sum of offset value 711*b* and value $h^{2,4}$ is less than zero, activation function output 719*c* may adjust it to zero. Other values of output feature map 713*c* may be computed as the learnable filter slides to overlap with different portions of input feature map 713*a*.

In a similar fashion, the convolutional layer may apply a learnable filter function and activation function to a three-dimensional input feature map in a convolutional layer. Here the weight matrix may be three dimensional. As in the two-dimensional case, the predictive model may be configured to convolve the weight matrix with the zero-padded input feature map to generate an intermediate map. But in the three-dimensional case the weight matrix may overlap with a volume of the zero-padded input feature map at each position. For example, when the input feature map includes a stack of three images, the weight matrix may be 3×3×3, and may overlap with a 3×3×3 volume of the zero-padded input feature map during the convolution operation. As in the two-dimensional case, the respective pixel values of the input feature map may be multiplied with the respective weights overlapping with them, and the multiplication results may be summed to derive a corresponding value in a three-dimensional intermediate map. This corresponding value may be summed with an offset value, and an activation function may be applied to the result to generate a three-dimensional output feature map.

A convolutional neural network may include stacks of convolutional layers comprising one or more convolutional layers. In some embodiments, these stacks may include between two and five convolutional layers. Furthermore, different stacks of convolutional layers may comprise differing numbers of convolutional layers. FIG. 7B illustrates the operation of convolutional layer(s) 720, an exemplary stack of convolutional layers. Convolutional layer(s) 720 may be configured to receive feature map(s) 721*a* and output feature map(s) 721*c*. Convolutional layer(s) 720 may include convolutional layer 723*a*, which may be configured to generate feature map(s) 721*b* using feature map(s) 721*a*, and convolutional layer 723*b*, which may be configured to generate feature map(s) 721*c* using feature map(s) 721*b*. The number of feature maps in each of feature map(s) 721*a*, feature map(s) 721*b*, and feature map(s) 721*c* may be predetermined.

In some embodiments, feature map(s) 721*a* may include one or more origin images of an object. For example, feature map(s) 721*a* may include T1-weighted MRI image(s), T2-weighted MRI image(s), and MRI image(s) generated using a contrast agent. As an additional example, feature map(s) 721*a* may comprise different slices in a stack of 2D images of the object. These slices may be adjacent. In various embodiments, feature map(s) 721*a* may include a stack of one or more feature maps generated by another component of the predictive model. For example, feature map(s) 721*a* may comprise a stack of sixty four feature maps generated by a previous convolutional layer of the predictive model.

Feature map(s) 721*b* may include feature maps generated by convolutional layer 723*a*. In some embodiments, convolutional layer 723*a* may generate these feature maps according to Eq. 1. For example, convolutional layer 723*a* may apply a learnable filter function and activation function to generate each feature map in feature map(s) 721*b*. Each learnable filter function may be described by a weight matrix and an offset value. Values of the weight matrix and the offset are parameters of the learnable filter, which can be learnt from data at the training stage of the convolutional neural network model. The number of parameters in the weight matrix may depend on the spatial size of the learnable filter function and the number of feature maps in feature map(s) 721*a*. For example, when input feature map(s) 721*a* includes l feature maps and the filter function is m×n in spatial size, the weight matrix may include m×n×l parameters. When output feature map(s) 721*b* includes k feature maps, k learnable filter functions may be used and accordingly, the overall number of parameters in convolutional layer 723*a* will be k×(m×n×l+1). As shown in FIG. 7B, feature maps in feature map(s) 721*b* and feature map(s) 721*a* may be the same spatial size. In various embodiments, the number of feature maps in feature map(s) 721*a* and feature map(s) 721*b* may differ. For example, feature map(s) 721*a* may include three feature maps, while feature map(s) 721*b* may include more or less feature maps.

Feature map(s) 721*b* may be provided as inputs to the next convolutional layer 723*b*, which generates feature map(s) 721*c*. Similar to convolutional layer 723*a*, convolutional layer 723*b* may generate these feature maps according to Eq. 1, including applying one or more learnable filter functions and activation functions. Again, the number of feature maps in feature map(s) 721*b* and feature map(s) 721*c* may be the same, or they may differ. For example, feature map(s) 721*b* may include 64 feature maps, while feature map(s) 721*b* may include 128 feature maps.

FIG. 7C illustrates the operation of an exemplary max pooling and unpooling layers of the predictive model. Pooling layers may receive and down-sample the input feature map received from a convolutional layer, generating an output feature map of reduced size. This output feature map may have lower spatial resolution than the input feature map, and consequent convolutional layers can then learn image features with greater spatial extent, or greater spatial invariance, than the image features learned by the preceding convolutional layer at the higher spatial resolution. Thus, the predictive model may use pooling layers to help learn features at different levels of spatial resolution, improving conversion accuracy. For example, a pooling layer may use a 2×2 window with a stride of two input feature values (i.e., a non-overlapping window) to down-sample the feature map by a factor of two in each dimension. It is contemplated that the stride may differ and the window used may be any other suitable size, such as 3×3, 4×4, 8×8, 16×16, 32×32, etc.

In some embodiments, as shown in FIG. 7C, the pooling layer may be a max-pooling layer, which selects a single value equal to the maximum value within a pooling window. In the example of FIG. 7C, the pooling window is a 2×2 window. Other suitable sizes are contemplated for the pooling window. FIG. 7C depicts a portion of a pooling layer 731*a*, showing the values within pooling window 733*a*. The predictive model may be configured to output the largest value within pooling window 733*a* (i.e., 0.8) to a corresponding location in post-downsampling feature map 735*a*, as indicated by the arrow connecting pooling layer 731*a* and post-downsampling feature map 735*a*. The predictive model may also be configured to store locations of the maximum values within pooling layer 731*a*. For example, the predictive model may be configured to store such locations in binary mask 737, as indicated by the arrow connecting pooling layer 731*a* and binary mask 737. Binary mask 737 may be the same size as pooling layer 731a, and may indicate which input features had the maximum value within each window. A pixel value of "1" (or "True") in binary mask 737 may indicate that a corresponding pixel of pooling layer 731a contains a maximum value within a window, and a pixel value of "0" (or "False") may likewise indicate that a corresponding pixel of the feature map does not contain that maximum value within a window. As shown in FIG. 7C, the pixels of binary mask 737 corresponding to the pixel values 0.3, 0.6 and 0.1 in pooling window 733a have a pixel value "0", because those pixel values are not the maximum pixel value in pooling window 733a, while the pixel of binary mask 737 corresponding to the pixel value 0.8 in pooling window 733a has a pixel value "1", because 0.8 was the maximum pixel value in pooling window 733a. The predictive model may be configured to provide this information concerning maximum value locations to unpooling layers, as indicated by the arrow connecting binary mask 737 and unpooling layer 731b.

Unpooling layers may increase the size of the input feature map by upsampling. This upsampling may increase the spatial resolution of a feature map, increasing the ability of image conversion system 400 to accurately depict high resolution details in the synthetic image. In some embodiments, each unpooling layer may use an unpooling window size of 2×2, matching the 2×2 pooling window used in the corresponding pooling layer. Thus, an unpooling layer may cause the size of the feature map to increase by a factor of two in each dimension. Other suitable sizes are contemplated for the unpooling window.

In some embodiments, as shown in FIG. 7C, the predictive model may be configured to relate a pixel value in pre-upsampling feature map 735b to a pixel value in unpooling layer 731b. As shown in FIG. 7C, a pixel in pre-upsampling feature map 735b may correspond to an unpooling window 733b in unpooling layer 731b. A binary mask may further define a correspondence between pixels in pre-upsampling feature map 735b and pixels in unpooling layer 731b. This binary mask may have been generated by a corresponding pooling layer. For example, binary mask 737 generated by corresponding pooling layer 731a may be used by unpooling layer 731b. As described above, binary mask 737 may indicate which pixel values of pooling layer 731a were stored in post-downsampling feature map 735a. As shown in FIG. 7C, the pixel in pre-upsampling feature map 735b with pixel value 0.7 may correspond to the top right pixel in unpooling window 733b, because the top right value of the corresponding portion of binary mask 737 has a value of "1." The predictive model may be configured to set this corresponding pixel in unpooling layer 731b to the pixel value of the pixel in pre-upsampling feature map 735b, as indicated by the arrow connecting pre-upsampling feature map 735b and unpooling layer 731b. The remaining elements of unpooling window 733b may be set to a predetermined value, such as zero.

FIGS. 7D and 7E depict neural network 700, an exemplary implementation of the predictive model used by image conversion system 400, consistent with the disclosed embodiments. Neural network 700 may be configured to convert digital images represented by matrices of values, each value corresponding to a pixel in the image. The size of the matrix may correspond to the spatial size of the image. For example, a 1024×1024 matrix may correspond to an image of 1024×1024 spatial size. The matrix representing the origin image and the generated matrix representing the synthetic image may have the same size (or spatial resolution). Unlike conventional methods that predict the synthetic image on a pixel-by-pixel basis (one value of the matrix at a time), the disclosed method predicts an entire synthetic image of an equal spatial size as the origin image (all values of the matrix at once).

As described herein, neural network 700 may comprise input 741 and output 751. In some embodiments, a spatial size (or spatial resolution) of input 741 and output 751 may be the same. For example, input 741 may receive at least one 1024×1024 pixel origin image and output 751 may output at least one 1024×1024 pixel calculated synthetic image. Neural network 700 may, however, process image data of other spatial sizes.

Input 741 of neural network 700 may be configured to accept one or more origin images. When training neural network 700 to convert 3D images, the accuracy of the neural network 700 may be increased when input 741 receives a stack of adjacent images, as the adjacent 2D images may contain dependent structure information. Dependent structure information may include spatially dependent relationships between the anatomical structures shown in the stack of adjacent 2D images. These spatially dependent relationships may be along the axis orthogonal to the anatomical plane of the 2D images. As a non-limiting example, the shape and type of an anatomical structure represented by a first set of pixels in a first image of the stack may also be represented by a second set of pixels in a second image adjacent to the first image. This is because the first and second images are spatially neighboring each other along the axis orthogonal to the anatomical plane. As a result, the two images will have some dependency or continuity of the anatomical structures shown in these images. Therefore, the shape, size, and/or type of an anatomical structure in one image may provide additional information of the shape, size, and/or type of the anatomical structure in another adjacent image along the same plane. The effect of dependent structure information may depend on various factors, such as the number of adjacent images in the stack, the anatomical structures depicted in the images, and/or the imaging modality used for obtaining the images.

In some embodiments, the input 741 may also be configured to receive multi-channel MRI images. For example, one or more first channels of input 741 may be configured to receive a T1-weighted MRI images and one or more second channels of input 741 may be configured to receive T2-weighted MRI images. As known in the art, T1 is the longitudinal relaxation constant and T2 is the transverse relaxation constant governing the rates at which excited protons in a tissues return to equilibrium. These rate constants differ from each other and differ between tissues. Depending on MRI imaging parameters, the contrast and brightness of a tissue in an MRI image may be predominantly determined by the T1 rate constant (a T1-weighted MRI image) or the T2 rate constant (a T2-weighted MRI image). Thus T1-weighted MRI images and T2-weighted MRI images convey different information about an imaged object. Neural network 700 may be configured to use the additional information provided by using a first channel of T1-weighted MRI images and another channel of T2-weighted MRI images to improve conversion accuracy. Additionally or alternatively, channels may be devoted to images associated with other tissue parameters known in the art, such as spin density, or to MRI images acquired using contrast agents.

As shown in FIGS. 7D and 7E, image data may flow from input 741 to output 751 through encoding stage 740 and decoding stage 750. Encoding stage 740 may be configured to extract feature maps from an input image. In some implementations, encoding stage 740 may not include fully-connected layers. A fully-connected layer is generally one in which every pixel of the input feature map contributes to each pixel of the output feature map. As recognized in the art, fully-connected layers require an extremely large number of parameters and generate features suited for image classification tasks. Such features provide little benefit in this application, and excluding fully-connected layers may reduce the number of parameters required to train the convolutional neural network. Decoding stage 750 may be configured to convert feature maps output from encoding stage 740 into a synthetic image with the same spatial resolution as the original image.

As shown in FIGS. 7D and 7E, neural network 700 may comprise stacks of convolutional layers (e.g., convolutional layer(s) 743a, and convolutional layer(s) 753a), pooling layers (e.g., pooling layer 745a), and unpooling layers (e.g., unpooling layer 755a). As described in FIGS. 7A and 7B, stacks of convolutional layers may be configured to generate output feature maps based on input feature maps (or origin images). As described in FIG. 7C, pooling layers may be configured to downsample feature maps, and unpooling layers may be configured to upsample feature maps.

As shown in FIGS. 7D and 7E, neural network 700 may be arranged in a hierarchy of levels of differing spatial resolution. Five such levels are depicted in FIGS. 7D and 7E, but neural network 700 may include additional levels or fewer levels. Each level may have an encoding and a decoding section (which combined over all levels include encoding stage 740 and decoding stage 750). Each level of spatial resolution in the hierarchy may be associated with feature maps of a certain spatial size, depending on the spatial size of the input image. With the exception of the lowest level, the output of the encoding section for each level may be provided to the input of the encoding section for the next level. For example, the output of convolutional layer(s) 743a on the highest level may be provided to the input of pooling layer 745a on the next lower level. With the exception of the highest level, the output of the decoding section may be provided to the input of the decoding section for the next highest level. For example, the output of convolutional layer(s) 753d on the second-to-lowest level may be provided to the input of unpooling layer 755c on the next higher level.

Furthermore, one or more layers in encoding stage 740 may be directly connected to a corresponding layer in decoding stage 750. For example, the final layer in convolutional layer(s) 743a may output one or more feature maps to decoding stage 750. These feature map(s) may be combined (e.g., stacked) with the output feature map of unpooling layer 755b to generate the input to convolutional layer 753b. FIGS. 7D and 7E indicate such direct connections between convolutional layer(s) 743a to convolutional layer(s) 743d and unpooling layer 755a to unpooling layer 755d, respectively. The provided feature maps are indicated in FIGS. 7D and 7E as the dashed portions of unpooling layer 755a to unpooling layer 755d. Direct connections between encoding stage 740 and decoding stage 750 may enable high resolution features learned in encoding stage 740 to be used in decoding stage 750. This may allow or improve the ability of decoding stage 750 to generate more accurate synthetic images. Such direct connections may also improve the flexibility of neural network 700. For example, neural network 700 may be trained to assign little weight to lower spatial resolution features when higher resolution features provided through the direct connections are sufficient to generate accurate synthetic images.

The highest level of neural network 700 may include an input 741, convolutional layer(s) 743a, unpooling layer 755a, convolutional layer(s) 753a, and output layer 759. In some embodiments, convolutional layer(s) 743a, convolutional layer(s) 753a, and output layer 759 may be stacks of one or more convolutional layers. For example, convolutional layer(s) 743a and convolutional layer(s) 753a may each include two to five convolutional layers. Alternatively, output layer 759 may include a single convolutional layer. As discussed with regards to FIGS. 7A and 7B, these convolutional layers may generate output feature maps by applying one or more learnable filter functions to their respective input feature maps. For example, the one or more convolutional layers comprising convolutional layer(s) 743a and convolutional layer(s) 753a may each apply between 50 and 100 (e.g., 64) learnable filter functions to generate a corresponding number of output feature maps.

The next-lower level of neural network 700 may include a pooling layer 745a, convolutional layer(s) 743b, unpooling layer 755b, and convolutional layer(s) 753b. In some embodiments, convolutional layer(s) 743b and convolutional layer(s) 753b may be stacks of one or more convolutional layers. For example, convolutional layer(s) 743b and convolutional layer(s) 753b may each include two to five convolutional layers. As discussed with regards to FIGS. 7A and 7B, these convolutional layers may generate output feature maps by applying one or more learnable filter functions to their respective input feature maps. For example, the one or more convolutional layers comprising convolutional layer(s) 743b and convolutional layer(s) 753b may each apply between 100 and 200 (e.g., 128) learnable filter functions to generate a corresponding number of output feature maps. Pooling layer 745a may correspond to unpooling layer 755a in the next-highest level. For example, pooling layer 745a may be configured to generate a binary mask indicating the locations of maximum values in its input feature layer, and provide these indications to unpooling layer 755a. Unpooling layer 755a may be configured to use the binary mask when upsampling its input feature map.

The next-lower level of neural network 700 may include a pooling layer 745b, convolutional layer(s) 743c, unpooling layer 755c, and convolutional layer(s) 753c. In some embodiments, convolutional layer(s) 743c and convolutional layer(s) 753c may be stacks of one or more convolutional layers. For example, convolutional layer(s) 743c and convolutional layer(s) 753c may each include two to six convolutional layers. As discussed with regards to FIGS. 7A and 7B, these convolutional layers may generate output feature maps by applying one or more learnable filter functions to their respective input feature maps. For example, the one or more convolutional layers comprising convolutional layer(s) 743c and convolutional layer(s) 753c may each apply between 150 and 300 (e.g., 256) learnable filter functions to generate a corresponding number of output feature maps. Pooling layer 745b may correspond to unpooling layer 755b in the next-highest level. For example, pooling layer 745b may be configured to generate indications of the locations of maximum values in its input feature map, and to provide these indications to unpooling layer 755b. Unpooling layer 755b may be configured to use these indications when upsampling the feature map.

The next-lower level of neural network 700 may include a pooling layer 745c, convolutional layer(s) 743d, unpooling layer 755d, and convolutional layer(s) 753d. In some embodiments, convolutional layer(s) 743d and convolutional layer(s) 753d may be stacks of one or more convolutional layers. For example, convolutional layer(s) 743d and convolutional layer(s) 753*d* may each include two to six convolutional layers. As discussed with regards to FIGS. 7A and 7B, these convolutional layers may generate output feature maps by applying one or more learnable filter functions to their respective input feature maps. For example, the one or more convolutional layers comprising convolutional layer(s) 743*d* and convolutional layer(s) 753*d* may each apply between 300 and 600 (e.g., 512) learnable filter functions to generate a corresponding number of output feature maps. Pooling layer 745*c* may correspond to unpooling layer 755*c* in the next-highest level. For example, pooling layer 745*c* may be configured to generate indications of the locations of maximum values in its input feature layer, and to provide these indications to unpooling layer 755*c*. Unpooling layer 755*c* may be configured to use these indications when upsampling the feature map.

The lowest level of neural network 700 may include a pooling layer 745*d*, convolutional layer(s) 743*e*, and convolutional layer(s) 753*e*. In some embodiments, convolutional layer(s) 743*e* and convolutional layer(s) 753*e* may be stacks of convolutional layers. For example, convolutional layer(s) 743*e* and convolutional layer(s) 753*e* may each include two to five convolutional layers. As discussed with regards to FIGS. 7A and 7B, these convolutional layers may generate output feature maps by applying one or more learnable filter functions to their respective input feature maps. For example, the one or more convolutional layers comprising convolutional layer(s) 743*e* and convolutional layer(s) 753*e* may each apply between 800 and 1200 (e.g., 1024) learnable filter functions to generate a corresponding number of output feature maps. Pooling layer 745*d* may correspond to unpooling layer 755*d* in the next-highest level. For example, pooling layer 745*d* may be configured to generate indications of the locations of maximum values in its input feature layer, and to provide these indications to unpooling layer 755*d*. Unpooling layer 755*d* may be configured to use these indications when upsampling the feature map.

Figure 7F:
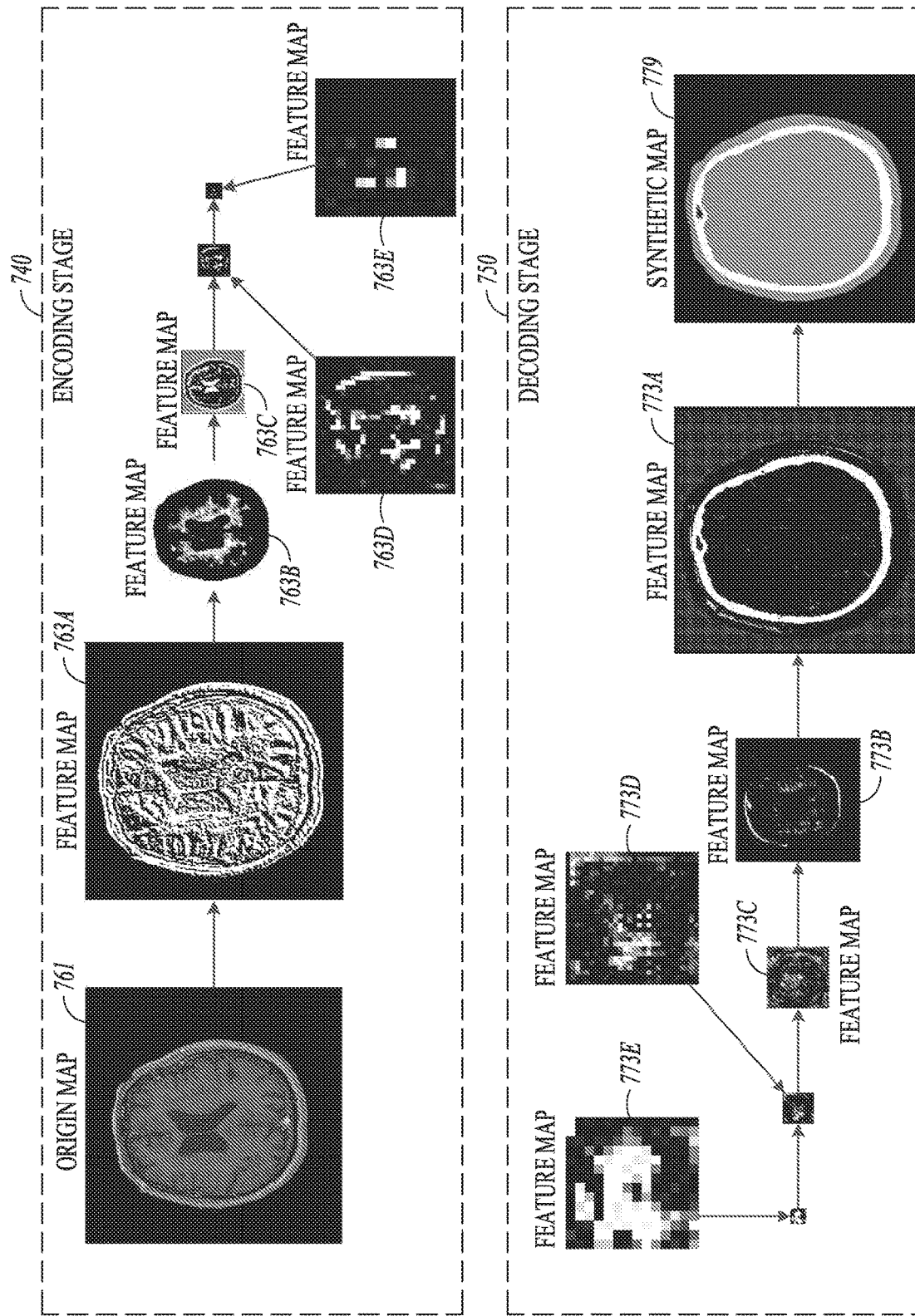
FIG. 7F depicts exemplary feature maps generated by selected layers of the neural network shown in FIGS. 7D and 7E, according to some embodiments of the present disclosure.

As described with regards to FIGS. 7D and 7E, one or more origin images (e.g., origin image 761) may be provided as input 741 to neural network 700. Neural network 700 may be configured to propagate input 741 through encoding stage 740 and decoding stage 750 to generate one or more destination images (e.g., destination image 769) as output 751. FIG. 7F depicts exemplary feature maps generated by selected layers of neural network 700 during steps of the encoding and decoding process. In particular, FIG. 7F depicts feature maps generated during each step of encoding stage 740, beginning with origin image 761 and ending with feature map 763*e*. As shown, the relative spatial size of these exemplary feature maps decreases during the encoding stage (enlarged versions of feature map 763*d* and feature map 763*e* are provided for ease of comprehension). These feature maps also depict the increasing spatial extent of the features in each map, and the decreasing spatial resolution of each map. FIG. 7E also depicts feature maps generated during each step of decoding stage 750, beginning with feature map 773*e* and ending with destination image 779. As shown, the relative spatial size of these exemplary feature maps increases during the decoding stage (enlarged versions of feature map 773*e* and feature map 773*d* are provided for ease of comprehension). These feature maps also depict the decreasing spatial extent of the features in each map, and the increasing spatial resolution of each map.

As a first encoding step, convolutional layer(s) 743*a* may be configured to receive one or more origin images and generate feature maps. As described above with regard to FIG. 7C, convolutional layer(s) 743*a* may comprise a stack of one or more convolutional layers. In some embodiments, convolutional layer(s) 743*a* may be configured to receive one or more origin images, such as origin image 761, and output feature maps, such as feature map 763*a*. As described above, the disclosed systems and methods are not limited to images of a particular spatial size. For example, in some embodiments, the spatial size of the one or more origin images may be greater than 128×128 pixels, such as 1024× 1024 pixels. In some embodiments, the one or more origin images may include at least one T1-weighted MRI image, T2-weighted MRI image, and MRI image generated using a contrast agent. As an additional example, the one or more origin images may include different slices in a stack of 2D images. In some embodiments, convolutional layer(s) 743*a* may be configured to output the feature maps to a next-lower level of encoding stage 740. This next-lower level of encoding stage 740 may include pooling layer 745*a* and convolutional layer(s) 743*b*. Convolutional layer(s) 743*a* may also be configured to output the feature maps directly to decoding stage 750.

As a second encoding step, pooling layer 745*a* may be configured to downsample the feature maps received from convolutional layer(s) 743*a*, generating downsampled feature maps with a smaller spatial size. Convolutional layer(s) 743*b* may be configured to receive these downsampled feature maps and generate output feature maps, such as feature map 763*b*. As shown, feature map 763*b* may have a smaller spatial size than feature map 763*a*. In some aspects, the spatial size of feature map 763*b* may be half the spatial size of feature map 763*a* in at least one dimension. In some embodiments, convolutional layer(s) 743*b* may be configured to output the feature maps to a next-lower level of encoding stage 740. This next-lower level of encoding stage 740 may include pooling layer 745*b* and convolutional layer(s) 743*c*. Convolutional layer(s) 743*b* may also be configured to provide the output feature maps directly to decoding stage 750.

As a third encoding step, pooling layer 745*b* may be configured to downsample the feature maps received from convolutional layer(s) 743*b*, generating downsampled feature maps with a smaller spatial size. Convolutional layer(s) 743*c* may be configured to receive these downsampled feature maps and generate output feature maps, such as feature map 763*c*. As shown, feature map 763*c* may have a smaller spatial size than feature map 763*b*. In some aspects, the spatial size of feature map 763*c* may be half the spatial size of feature map 763*b* in at least one dimension. In some embodiments, convolutional layer(s) 743*c* may be configured to output the feature maps to a next-lower level of encoding stage 740. This next-lower level of encoding stage 740 may include pooling layer 745*c* and convolutional layer(s) 743*d*. Convolutional layer(s) 743*c* may also be configured to provide the output feature maps directly to decoding stage 750.

As a fourth encoding step, pooling layer 745*c* may be configured to downsample the feature maps received from convolutional layer(s) 743*c*, generating downsampled feature maps with a smaller spatial size. Convolutional layer(s) 743*d* may be configured to receive these downsampled feature maps and generate output feature maps, such as feature map 763*d*. As shown, feature map 763*d* may have a smaller spatial size than feature map 763*c*. In some aspects, the spatial size of feature map 763*d* may be half the spatial size of feature map 763*c* in at least one dimension. In some embodiments, convolutional layer(s) 743*d* may be configured to output the feature maps to the lowest level of encoding stage 740. This lowest level of encoding stage 740 may include pooling layer 745d and convolutional layer(s) 743e. Convolutional layer(s) 743d may also be configured to provide the output feature maps directly to decoding stage 750.

As a fifth encoding step, pooling layer 745d may be configured to downsample the feature maps received from convolutional layer(s) 743d, generating downsampled feature maps with a smaller spatial size. Convolutional layer(s) 743e may be configured to receive these downsampled feature maps and generate output feature maps, such as feature map 763e. As shown, feature map 763e may have a smaller spatial size than feature map 763d. In some aspects, the spatial size of feature map 763e may be half the spatial size of feature map 763d in at least one dimension. In some embodiments, convolutional layer(s) 743e may be configured to provide these output feature maps to the lowest level of decoding stage 750.

In a first decoding step, convolutional layer(s) 753e may be configured to use the feature maps received from convolutional layer(s) 743e to generate output feature maps, such as feature map 773e. In some embodiments, convolutional layer(s) 753e may be configured to provide these output feature maps to a higher level of decoding stage 750. This higher level of decoding stage 750 may include unpooling layer 755d and convolutional layer(s) 753d.

In a second decoding step, unpooling layer 755d may be configured to upsample the feature maps received from convolutional layer(s) 753e, generating upsampled feature maps with increased spatial size. As described above with regard to FIG. 7C, unpooling layer 755d may use binary masks generated by pooling layer 745d to assign values in the feature maps received from convolutional layer(s) 753e to corresponding upsampled feature maps. Convolutional layer(s) 753d may be configured to use the upsampled feature maps received from unpooling layer 755d to generate output feature maps, such as feature map 773d. In some aspects, convolutional layer(s) 753d may also use feature maps received from convolutional layer(s) 743d to generate the output feature maps. For example, convolutional layer(s) 753d may be configured to apply one or more learnable filter functions to a stack of feature maps comprising the feature maps received from convolutional layer(s) 743d and the upsampled feature maps received from unpooling layer 755d. In some embodiments, the output feature maps generated by convolutional layer(s) 753d may be provided by convolutional layer(s) 753d to a higher level of decoding stage 750. This higher level of decoding stage 750 may include unpooling layer 755c and convolutional layer(s) 753c.

In a third decoding step, unpooling layer 755c may be configured to upsample the feature maps received from convolutional layer(s) 753d, generating upsampled feature maps with increased spatial size. As described above with regard to FIG. 7C, unpooling layer 755c may use binary masks generated by pooling layer 745c to assign values in the feature maps received from convolutional layer(s) 753d to corresponding upsampled feature maps. Convolutional layer(s) 753c may be configured to use the upsampled feature maps received from unpooling layer 755c to generate output feature maps, such as feature map 773c. In some aspects, convolutional layer(s) 753c may also use feature maps received from convolutional layer(s) 743c to generate the output feature maps. For example, convolutional layer(s) 753c may be configured to apply one or more learnable filter functions to a stack of feature maps comprising the feature maps received from convolutional layer(s) 743c and the upsampled feature maps received from unpooling layer 755c. In some embodiments, the output feature maps generated by convolutional layer(s) 753c may be provided by convolutional layer(s) 753c to a higher level of decoding stage 750. This higher level of decoding stage 750 may include unpooling layer 755b and convolutional layer(s) 753b.

In a fourth decoding step, unpooling layer 755b may be configured to upsample the feature maps received from convolutional layer(s) 753c, generating upsampled feature maps with increased spatial size. As described above with regard to FIG. 7C, unpooling layer 755b may use binary masks generated by pooling layer 745b to assign values in the feature maps received from convolutional layer(s) 753c to corresponding upsampled feature maps. Convolutional layer(s) 753b may be configured to use the upsampled feature maps received from unpooling layer 755b to generate output feature maps, such as feature map 773b. In some aspects, convolutional layer(s) 753b may also use feature maps received from convolutional layer(s) 743b to generate the output feature maps. For example, convolutional layer(s) 753b may be configured to apply one or more learnable filter functions to a stack of feature maps comprising the feature maps received from convolutional layer(s) 743b and the upsampled feature maps received from unpooling layer 755b. In some embodiments, the output feature maps generated by convolutional layer(s) 753b may be provided by convolutional layer(s) 753b to the highest level of decoding stage 750. This highest level of decoding stage 750 may include unpooling layer 755a, convolutional layer(s) 753a, and output layer 759.

In a fifth decoding step, unpooling layer 755a may be configured to upsample the feature maps received from convolutional layer(s) 753b, generating upsampled feature maps with increased spatial size. As described above with regard to FIG. 7C, unpooling layer 755a may use binary masks generated by pooling layer 745a to assign values in the feature maps received from convolutional layer(s) 753b to corresponding upsampled feature maps. Convolutional layer(s) 753a may be configured to use the upsampled feature maps received from unpooling layer 755a to generate output feature maps, such as feature map 773a. In some aspects, convolutional layer(s) 753a may also use feature maps received from convolutional layer(s) 743a to generate the output feature maps. For example, convolutional layer(s) 753a may be configured to apply one or more learnable filter functions to a stack of feature maps comprising the feature maps received from convolutional layer(s) 743a and the upsampled feature maps received from unpooling layer 755a. In some embodiments, output layer 759 may be configured to use the output feature maps received from convolutional layer(s) 753a to generate at least one destination image, such as destination image 779. In some embodiments, the at least one destination image may be provided to output 751.

In the exemplary embodiment shown in FIGS. 7D and 7E, neural network 700 may include 27 convolutional layers, with over 30 million parameters for converting a three channel image. This exemplary arrangement is not intended to be limiting. For example, the number of layers in neural network 700 between encoding stage 740 and decoding stage 750 may range from about 10 to a few hundred (e.g., 500). As the number of layers increases, the number of model parameters also increases, providing better accuracy in prediction. However, a large number of layers may also result in increased computational cost, especially during the training stage. The suitable number of layers may change as the computational power of processors advances. Similarly, neural network 700 may include more or fewer levels of spatial resolution. In some embodiments, a different number of input channels may be used or a different image size may be used.

Figure 8:
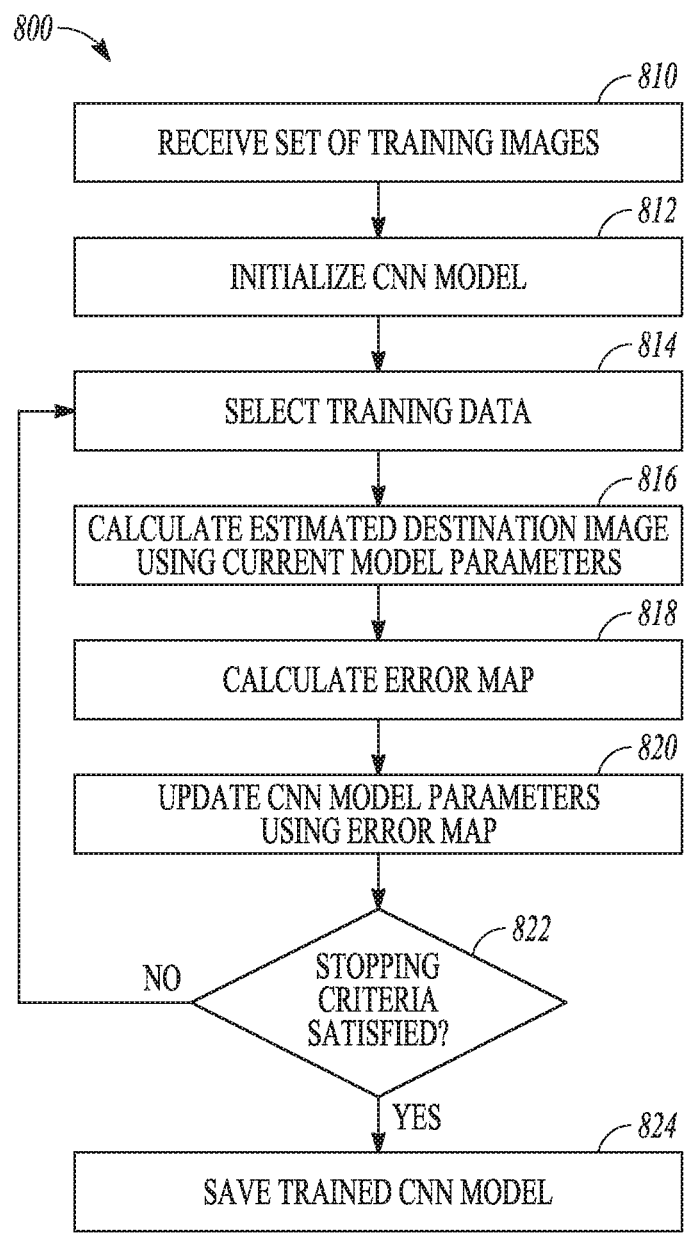
FIG. 8 is a flowchart illustrating an exemplary training process for training a CNN model, according to some embodiments of the present disclosure.

FIG. 8 is a flowchart illustrating an exemplary training process 800 for training neural network 700, consistent with disclosed embodiments. In some embodiments, training process 800 may be performed by training unit 430, described above, to learn model parameters θ={W$_1$, b$_1$, W$_2$, b$_2$, . . . } of neural network 700. Training process 800 may start when training unit 430 receives a set of training images (Step 810). As described above, the set of training images may include one or more origin images acquired using a first imaging modality and corresponding destination images acquired using a second imaging modality. For example, the training images may include single- or multi-channel MRI images of an anatomical area of a patient, such as a head, torso, abdomen, and/or limbs. In some embodiments, the corresponding destination images may be acquired by a CT scan of the same or similar anatomical area of the patient.

As shown in FIG. 8, training unit 430 may initialize the predictive model in step 812. For example, training unit 430 may initialize an iteration index for training the CNN model, e.g., to zero. In some embodiments, training unit 430 may also initialize the parameters of neural network 700. For example, convolutional layer weights may be initialized to random values, and/or convolutional layer biases may be initialized to zero. In some embodiments, training unit 430 may initialize the parameters of encoding stage 730 using parameters from pre-trained models. For example, training unit 430 may borrow weights from models trained for other tasks, such as image classification. This may enable image conversion system 400 to exploit the transfer learning characteristics of neural networks to speed up convergence on an acceptable solution.

Steps 814 through 822 may be performed iteratively until one or more stopping criteria are met (e.g., the iterative process converges according to predefined criteria). At each iteration, a new batch of training data may be randomly selected and used for training the CNN model until the maximum number of iterations is reached. In some embodiments, each batch may include 30-60 sets of training image. For example, each batch may include approximately 50 pairs of origin images and destination images.

In step 814, training unit 430 may be configured to select a batch of training data. In some embodiments, this training data may be selected randomly from the training data stored in database 410. Training unit 430 may be optionally configured to pre-process the training data. For example, training unit 430 may be configured to receive one or more training images 412 from database 410 and process them to remove certain image features, consistent with process 600 described above. In step 816, training unit 430 may be configured to calculate a synthetic image according to the current parameters of neural network 700 for each set of training images. In step 818, training unit 430 may be configured to generate an error map (e.g., as described above with respect to FIG. 2) based on the calculated synthetic image and the training data. For example, when the training data includes an origin image and a corresponding destination image, training unit 430 may be configured to generate an error map as a difference between the synthetic image and the destination image.

In step 820, training unit 430 may be configured to determine or update parameters of neural network 700 based on the error map generated by step 818. For example, backpropagation algorithms known to those of skill in the art may be used to determine or update parameters of neural network 700. In some embodiments, the backpropagation algorithm may be configured to minimize a loss function with respect to the parameters of neural network 700. For example, the backpropagation algorithm may update model parameters θ=(θ$_1$, θ$_2$, . . . , θ$_L$) to reduce the value of the loss function. One of skill in the art would be familiar with various loss functions that training unit 430 may implement, such as the mean absolute error (MAE) of the model prediction, which may be determined as follows:

$$E(\theta) = \frac{1}{n}\sum_{i=1}^{n}|y_i(\theta) - z_i| \qquad \text{Eq. 2}$$

where $y_i(\theta)$ indicates the calculated CT intensity value at each voxel of the synthetic image, $z_i$ denotes the CT intensity value at each voxel of the destination image (e.g., the true value), n is the total number of image voxels, and $E(\theta)$ represents the MAE. Using the MAE as the loss function may improve learning, making the learning process robust to outliers such as noise and artifacts in the training data. Alternatively, training unit 430 may be configured to use the mean squared error (MSE) of the model prediction, which may be determined as follows:

$$E(\theta) = \frac{1}{n}\sum_{i=1}^{n}|y_i(\theta) - z_i|^2 \qquad \text{Eq. 3}$$

Here, $E(\theta)$ represents the MSE.

The backpropagation algorithm may be used to compute the gradient of the loss function with respect to the model parameters (θ), such as the weights $W_k$ of the convolution filters and offset values b. The model parameters may then be updated iteratively by using a stochastic gradient descent algorithm. In some embodiments, batch normalization may be performed after each convolutional layer to reduce internal covariant shift.

Simple data augmentation may also be performed to artificially increase the number of training data during model training. In such data augmentation, new pairs of origin and destination images may be created through a random translation of pixels or flipping of images in each spatial dimension for each pair of MR and CT images. By using such data augmentation, exemplary embodiments consistent with the disclosure may increase the amount of training data and thus generate a more highly trained prediction model within training unit 430, leading to more accurate synthetic images generated by the model.

In step 822, training unit 430 may be configured to determine whether stopping criteria have been satisfied. Various stopping criteria may be used, such as a predetermined maximum number of iterations or a predetermined image quality measure (e.g., a loss function value indicating that the difference between the estimated synthetic image and the destination image is sufficiently small). For example, training unit 430 may be configured to determine whether an index is equal to or greater than the predetermined maximum number of iterations. Additionally or alternatively, training unit 430 may be configured to determine whether the accuracy of the synthetic image meets or exceeds an expected accuracy, e.g., by determining whether the loss function is smaller than certain threshold criteria. If training unit 430 determines that the stopping criteria have been not satisfied, the training process 800 may return to step 814. If training unit 430 determines that the stopping criteria has been satisfied, the training process 800 may proceed to step 824. In step 824, training unit 430 may be configured to store the updated version of neural network 700 for later use by image conversion unit 440.

Figure 9A:
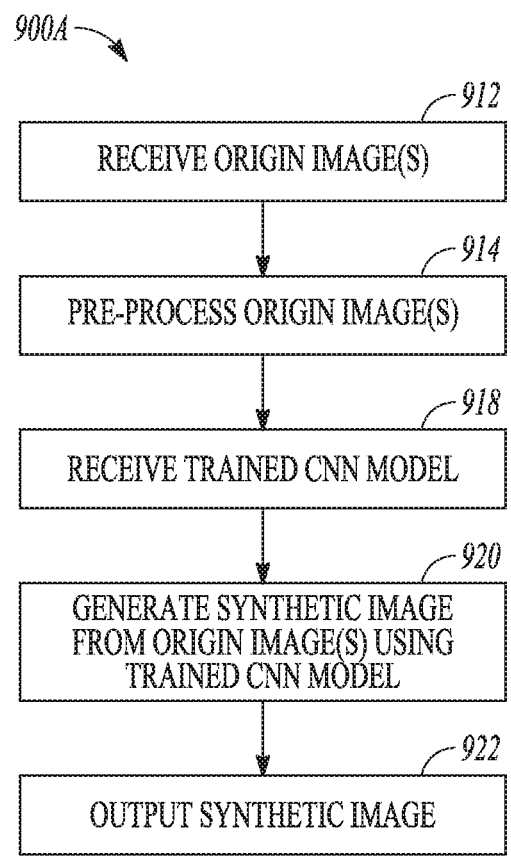
FIG. 9A is a flowchart illustrating an exemplary image conversion process using a trained CNN model obtained through the process of FIG. 8, according to some embodiments of the present disclosure.

FIG. 9A is a flowchart illustrating an exemplary image conversion process 900A using a trained convolutional neural network (e.g., neural network 700) obtained through process 800 of FIG. 8, according to some embodiments of the present disclosure. Image conversion process 900A may be performed by image conversion unit 440. In an embodiment, image conversion unit 440 may be configured to generate synthetic images from origin images acquired using the same imaging modality as the training images. For example, when neural network 700 is trained on MRI images, the image conversion unit 440 may be configured to generate synthetic images based on MRI images. Similarly, when neural network 700 is trained on single-channel MRI images, image conversion unit 440 may be configured to use the same type of single-channel MRI images (e.g., T1-weighted images). When neural network 700 is trained on multi-channel MRI images, image conversion unit 440 may be configured to use the same type of multi-channel MRI images.

As shown in FIG. 9A, process 900A may start when image conversion unit 440 receives one or more origin image in step 912. In some aspects, image conversion unit 440 may be configured to receive one or more origin images from image database 420, another component of image conversion system 400, or another system. In step 914, image conversion unit 440 may be optionally configured to preprocess the one or more origin images, consistent with process 600 described above, to remove artifacts associated with the origin images in order to increase the accuracy of the conversion process.

Image conversion unit 440 may be configured to receive neural network 700 in step 918. In some aspects, neural network 700 may be received from training unit 430, another component of image conversion system 400, or another system. Image conversion unit 440 may be configured to calculate one or more synthetic images using neural network 700 in step 920. Image conversion unit 440 may then output, in step 922, the one or more synthetic images. Outputting may include displaying a representation of one or more synthetic images for further analysis or observation, storing the one or more synthetic images in a non-transitory medium, or providing the one or more synthetic images to a computer process, program, and/or application. The non-transitory medium and computer process, program, and/or application may be on a remote system.

Process 900A may be performed to convert both 2D and 3D origin images. In case of converting 3D images, neural network 700 may be modified to generate 3D synthetic images. As described above, input 731 of neural network 700 may be configured to accept a stack of adjacent 2D images selected from the 3D origin image. Similarly, output layer 749 of neural network 700 may be configured to generate a corresponding number of adjacent synthetic images, which can be assembled into a 3D synthetic image. In some embodiments, a 3D origin image may be divided into stacks of 2D origin images. In some embodiments, the stacks of origin images may overlap. For example, the first stack may include the first through third image slices, the second stack may include the second through fourth image slices, and the third stack may include the third through fifth image slices. Image conversion unit 440 may then be configured to convert these stacks of origin images to corresponding stacks of synthetic images. For example, when the stack of images include three images, image conversion unit 440 may be configured to also generate three synthetic images corresponding to each of three origin images in the stack. The stacks of synthetic images may also overlap, consistent with the stack of origin images. As a result, for a given slice in the 3D synthetic images, multiple 2D synthetic images may be generated. These multiple synthetic images may be fused to derive one synthetic image for the slice. Various rules may be used for fusion. For example, the multiple images may be averaged, or the median values may be used, etc.

Figure 9B:
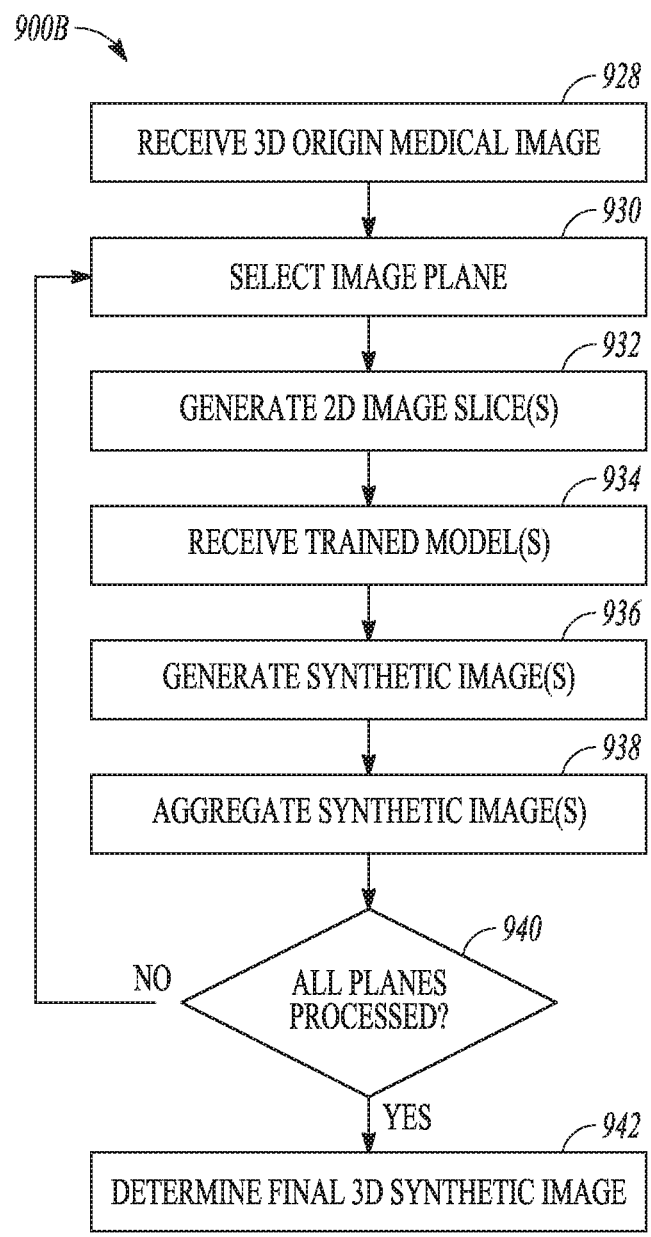
FIG. 9B is a flowchart illustrating an exemplary 3D image conversion process using at least one trained CNN model obtained through the process of FIG. 8, according to some embodiments of the present disclosure.

FIG. 9B depicts an exemplary flowchart illustrating a 3D image conversion process 900B, consistent with disclosed embodiments. In some embodiments, process 900B may be performed by image conversion unit 440. Process 900B begins in step 928 by having image conversion unit 440 configured to receive one or more 3D origin images. The 3D images may be received from image database 420 or from another component of image conversion system 400. The 3D images may include images of a head, torso, abdomen, limbs, or any another anatomical area, either in part or in whole, of a patient.

In step 930, image conversion unit 440 may be configured to select an anatomical plane of a received 3D origin image. In step 932, image conversion unit 440 may be configured to generate one or more stacks of 2D origin images based on the received 3D image and the selected plane. For example, image conversion unit 440 may be configured to select among the three anatomical planes, including the axial plane, sagittal plane, and coronal plane. Image conversion unit 440 may be configured to generate 2D origin images from the received 3D origin image along the selected anatomical plane. In some aspects, image conversion unit 440 may be configured to generate a sequence of individual origin images, or a sequence of stacks of origin images.

In step 934, image conversion unit 440 may be configured to receive a neural network (e.g., neural network 700). The received neural network may correspond to the selected anatomical plane. For example, the received neural network may have been trained with images (or stacks of images) along the selected anatomical plane. Such images (or stacks of images) along the selected anatomical plane may collectively comprise dependent structure information for an axis orthogonal to the selected anatomical plane. Because the received neural network has been trained using images along the selected anatomical plane, this neural network may be capable of using this dependent structure information to improve conversion efficiency. For example, the parameters or weights of the received neural network may reflect this dependent structure information. In response to a change in the selected anatomical plane (e.g., sagittal to coronal), image conversion unit 440 may be configured to receive another neural network corresponding to the newly selected anatomical plane. For example, image conversion unit 440 may receive an axial neural network, a coronal neural network, or a sagittal neural network, according to the selected plane. Just as the previously received neural network was capable of using dependent structure information for an axis orthogonal to the previously selected anatomical plane to improve conversion efficiency, the newly received neural network may be capable of using dependent structure information for an axis orthogonal to the newly selected anatomical plane to improve conversion efficiency. In some embodiments, image conversion unit 440 may be configured to receive a neural network trained with images (or stacks of images) along multiple planes (e.g., multiple anatomical planes, such that the stack may include a coronal images, sagittal images; or the stack may include axial images and a sagittal images, etc.). Accordingly, image conversion unit 440 may be configured to use this neural network to generate synthetic images from origin images along any selected anatomical plane or multiple anatomical planes.

In step 936, image conversion unit 440 may be configured to generate corresponding synthetic images, or stacks of synthetic images using the received neural network. As described above, conversion efficiency may be improved using neural networks trained using images (or stacks of images) along a particular anatomical plane, as these networks may use dependent structure information specific to that particular anatomical plane. Image conversion unit 440 may repeat step 936 until all selected origin images, or selected stacks of origin images have been converted to synthetic images.

In some embodiments, image conversion unit 440 may perform step 930 after step 934. For instance, the trained neural network received by image conversion unit 440 may be trained using 2D origin images along multiple planes (e.g., all three planes). In such a case, image conversion unit 440 may be configured to iteratively select each of the different planes and generate 2D origin images along the selected plane. These 2D origin images along the three planes may be independently input to the neural network 700 to generate synthetic images along the respective planes. For example, axial 2D origin images may be input into the neural network 700, which outputs axial synthetic images. Sagittal 2D origin images may be input into the neural network 700, resulting in sagittal synthetic images. And finally, coronal 2D origin images may be input into the neural network 700 resulting in coronal synthetic images. Alternatively, the 2D origin images of all three planes may be combined into a single sequence (e.g., axial 2D origin images followed by the sagittal 2D origin images, then followed by the coronal 2D origin images), and input to the same neural network 700, which is trained using images stacked from the three-planes.

In step 938, image conversion unit 440 may be configured to aggregate the resulting 2D synthetic images into a 3D synthetic image. Such aggregation may include stacking the synthetic images along an axis orthogonal to the selected plane, to obtain a 3D synthetic image.

In step 940, image conversion unit 440 may determine whether all planes of the 3D origin image have been processed. For example, image conversion unit 440 may continue to process each plane until a predefined 3D image volume has been processed. Alternatively, image conversion unit 440 may continue to process until a predefined number of 2D planar images have been processed. If all the planes have been processed based on the criteria used in step 940, then process 900B continues to step 942. If the planes have not been processed, image conversion unit 440 may be configured to return to step 930 and select another image plane for processing.

Because the 3D synthetic image of each plane provides a pixel value to any given pixel in the 3D image, every pixel may have three different pixel values. The 3D synthetic images, therefore, may be combined to determine the final 3D synthetic image. In step 942, image conversion unit 440 may be configured to determine a final 3D synthetic image. Image conversion unit 440 may be configured to determine the final 3D synthetic image by combining (e.g., as known in the art as "fusing") the 3D synthetic images corresponding to each selected plane (e.g., the axial, sagittal, and coronal planes). In some embodiments, the value of a voxel of the fused 3D synthetic image may be an average value. For example, if the three fused 3D synthetic images were to have CT values of 70, 80, and 30, respectively, then the voxel may then have an average CT value of 60. As another example, the median voxel value, e.g., 70 in the above example, may be used. Other methods of combining the values of the voxels may be used, and the above example is not intended to be limiting. In this manner, the dependent structure information specific to each anatomical plane may be incorporated into the final 3D synthetic image.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface.

A machine or computer-readable storage medium may include one or more non-transitory media (e.g., a centralized or distributed database, and/or associated caches and servers). Such a machine or computer-readable storage medium may store computer-executable instructions or data that may cause a machine to perform the functions or operations described. Such a machine or computer-readable storage medium may include any mechanism that stores information in a form accessible by a machine (e.g., computing device, electronic system, and the like), such as recordable/non-recordable medium (e.g., read only memory (ROM), random access memory (RAM), magnetic disk storage medium, optical storage medium, flash memory devices, and the like). For example, the term "machine-readable storage medium" or "computer-readable storage medium" shall accordingly be taken to include, but not be limited to, solid-state memories, optical, and magnetic medium.

A communication interface may include any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

What is claimed is:

1. A computer-implemented method for generating a synthetic image of an anatomical portion based on an origin image of the anatomical portion acquired by an imaging device using a first imaging modality, the method comprising:

receiving the origin image of the anatomical portion acquired by the imaging device using the first imaging modality, wherein the origin image includes a three-dimensional image;

obtaining a plurality of stacks of two-dimensional images from the three-dimensional image;

receiving a convolutional neural network model trained for generating a synthetic image based on origin image data; and generating, by at least one processor; the synthetic image from the origin image through use of the convolutional neural network model, the synthetic image resembling a second imaging modality depiction of the anatomical portion, wherein the second imaging modality provides imaging data that differs in format from imaging data provided by the first imaging modality, and wherein generating the synthetic image includes:
generating a plurality of stacks of synthetic two-dimensional images from the plurality of stacks of two-dimensional images, using the convolutional neural network model; and
determining the synthetic image by aggregating the plurality of stacks of synthetic two-dimensional images.

2. The method of claim 1, wherein the first imaging modality is Magnetic Resonance Imaging, and the second imaging modality is Computed Tomography.

3. The method of claim 1, wherein the first imaging modality and the second imaging modality are selected from the group of Magnetic Resonance Imaging, Computed Tomography, ultrasound imaging, Positron Emission Tomography, and Single-Photon Emission Computed Tomography.

4. The method of claim 1, further comprising:
receiving a plurality of training origin images acquired using the first imaging modality;
receiving a plurality of training destination images acquired using the second imaging modality, each training destination image corresponding to a training origin image;
determining a convolutional neural network architecture; and
training the convolutional neural network model using the training origin images and corresponding training destination images.

5. The method of claim 1, wherein the synthetic image includes a stack of two-dimensional images.

6. The method of claim 1, wherein the origin image is provided in a three-dimensional volume and the synthetic image is provided in a three-dimensional volume.

7. The method of claim 1,
wherein obtaining the plurality of stacks of two-dimensional images comprises selecting a plurality of stacks of adjacent two-dimensional images from the three-dimensional image; and
wherein generating the plurality of stacks of synthetic two-dimensional images comprises generating respective stacks of synthetic two-dimensional images from the plurality of stacks of adjacent two-dimensional images using the convolutional neural network model.

8. The method of claim 7,
wherein obtaining the plurality of stacks of two-dimensional images comprises creating a first stack of two-dimensional images from a first plane of the three-dimensional image and a second stack of two-dimensional images from a second plane of the three-dimensional image; and
wherein generating the plurality of stacks of synthetic two-dimensional images comprises generating a first stack and a second stack of synthetic two-dimensional images from the first stack and the second stack of two-dimensional images using the convolutional neural network model.

9. The method of claim 7, wherein the origin image includes multi-channel images of the anatomical portion acquired using different acquisition settings or using different acquisition channels of the imaging device.

10. The method of claim 4, wherein training the convolutional neural network model further includes:
generating synthetic images from the training origin images using the convolutional neural network model;
determining a difference between the synthetic images and the corresponding training destination images; and
updating model parameters of the convolutional neural network model based on the difference.

11. The method of claim 10, wherein the training is completed when a difference between a respective synthetic image and a respective destination image is smaller than a predetermined threshold.

12. The method of claim 10, wherein the difference is measured by a loss function calculated based on the synthetic image and the destination image.

13. A system for generating a synthetic image of an anatomical portion based on an origin image of the anatomical portion acquired by an imaging device using a first imaging modality, the system comprising:
an input interface configured to:
receive the origin image of the anatomical portion acquired by the imaging device using the first imaging modality, wherein the origin image includes a three-dimensional image, and wherein the three-dimensional image provides a plurality of stacks of two-dimensional images; and
receive a convolutional neural network model trained for generating a synthetic image based on origin image data; and
at least one storage device configured to store the origin image and the convolutional neural network model; and
an image processor configured to generate the synthetic image from the origin image through use of the convolutional neural network model, the synthetic image resembling a second imaging modality depiction of the anatomical portion, wherein the second imaging modality provides imaging data that differs in format from imaging data provided by the first imaging modality, and wherein the image processor is configured to generate the synthetic image with operations to:
generate a plurality of stacks of synthetic two-dimensional images from the plurality of stacks of two-dimensional images, using the convolutional neural network model; and
determine the synthetic image by aggregating the plurality of stacks of synthetic dimensional images.

14. The system of claim 13, wherein the origin image includes multi-channel images of the anatomical portion acquired using different acquisition settings or using different acquisition channels of the imaging device.

15. The system of claim 13, wherein the first imaging modality is Magnetic Resonance Imaging, and the second imaging modality is Computed Tomography.

16. The system of claim 13, wherein the first imaging modality and the second imaging modality is selected from among the group of Magnetic Resonance Imaging, Computed Tomography, ultrasound imaging, Positron Emission Tomography, and Single-Photon Emission Computed Tomography.

17. The system of claim 13, wherein the input interface is further configured to:
receive a plurality of training origin images acquired using the first imaging modality;
receive a plurality of training destination images acquired using the second imaging modality, each training destination image corresponding to a training origin image; and wherein the image processor is further configured to:
train the convolutional neural network model using the training origin images and corresponding training destination images.

18. The system of claim 13, wherein the synthetic image includes a stack of two-dimensional images.

19. The system of claim 13, wherein the origin image is provided in a three-dimensional volume and the synthetic image is provided in a three-dimensional volume.

20. The system of claim 13, wherein the image processor is further configured to:
select a plurality of stacks of adjacent two-dimensional images from the three-dimensional image; and
generate the plurality of stacks of synthetic two-dimensional images by generating respective stacks of synthetic two-dimensional images from the plurality of stacks of adjacent two-dimensional images using the convolutional neural network model.

21. The system of claim 13, wherein the image processor is further configured to:
create a first stack of two-dimensional images from a first plane of the three-dimensional image and a second stack of two-dimensional images from a second plane of the three-dimensional image; and
generate the plurality of stacks of synthetic two-dimensional images by generating a first stack and a second stack of synthetic two-dimensional images from the first stack and the second stack of two-dimensional images using the convolutional neural network model.

22. A non-transitory computer-readable medium comprising instructions that, when executed by at least one processor, cause the at least one processor to generate a synthetic image of an anatomical portion based on an origin image of the anatomical portion acquired by an imaging device using a first imaging modality, with operations comprising:
receiving the origin image of the anatomical portion acquired by the imaging device using the first imaging modality, wherein the origin image includes a three-dimensional image;
obtaining a plurality of stacks of two-dimensional images from the three-dimensional image;
receiving a convolutional neural network model trained for generating a synthetic image based on the origin image; and
generating the synthetic image from the origin image through use of the convolutional neural network model, the synthetic image resembling a second imaging modality depiction of the anatomical portion, wherein the second imaging modality provides imaging data that differs in format from imaging data provided by the first imaging modality, and wherein generating the synthetic image includes:
generating a plurality of stacks of synthetic two-dimensional mages from the plurality of stacks of two-dimensional images, using the convolutional neural network model; and
determining the synthetic image by aggregating the plurality of stacks of synthetic two-dimensional images.

23. The non-transitory computer-readable medium of claim 22, the operations further comprising:
receiving a plurality of training origin images acquired using the first imaging modality;
receiving a plurality of training destination images acquired using the second imaging modality, each training destination image corresponding to a training origin image;
determining a convolutional neural network architecture; and
training the convolutional neural network model using the training origin images and corresponding training destination images.

24. The non-transitory computer-readable medium of claim 22,
wherein obtaining the plurality of stacks of two-dimensional images comprises selecting a plurality of stacks of adjacent two-dimensional images from the three-dimensional image; and
wherein generating the plurality of stacks of synthetic two-dimensional images comprises generating respective stacks of synthetic two-dimensional images from the plurality of stacks of adjacent two-dimensional images using the convolutional neural network model.

25. The non-transitory computer-readable medium of claim 22, wherein obtaining the plurality of stacks of two-dimensional images comprises creating a first stack of two-dimensional images from a first plane of the three-dimensional image and a second stack of two-dimensional images from a second plane of the three-dimensional image; and
wherein generating the plurality of stacks of synthetic two-dimensional images comprises generating a first stack and a second stack of synthetic two-dimensional images from the first stack and the second stack of two-dimensional images using the convolutional neural network model.

* * * * *

UNITED STATES PATENT AND TRADEMARK OFFICE
CERTIFICATE OF CORRECTION

PATENT NO. : 10,867,417 B2  
APPLICATION NO. : 16/330648  
DATED : December 15, 2020  
INVENTOR(S) : Xiao Han Page 1 of 1

It is certified that error appears in the above-identified patent and that said Letters Patent is hereby corrected as shown below:

In the Claims

In Column 44, Line 65, in Claim 1, delete "processor;" and insert --processor,-- therefor In Column 45, Line 49, in Claim 8, delete "claim 7," and insert --claim 1,-- therefor In Column 45, Line 62, in Claim 9, delete "claim 7," and insert --claim 1,-- therefor In Column 46, Line 46, in Claim 13, delete "dimensional" and insert --two-dimensional-- therefor In Column 48, Line 6, in Claim 22, delete "mages" and insert --images-- therefor Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*